(12) United States Patent
Jackson et al.

(10) Patent No.: US 6,308,570 B1
(45) Date of Patent: Oct. 30, 2001

(54) METHOD AND APPARATUS FOR ULTRASONIC CHARACTERIZATION THROUGH THE THICKNESS DIRECTION OF A MOVING WEB

(75) Inventors: Theodore Jackson, Atlanta; Maclin S. Hall, Marietta, both of GA (US)

(73) Assignee: Institute of Paper Science and Technology, Inc., Atlanta, GA (US)

( * ) Notice: Subject to any disclaimer, the term of this patent is extended or adjusted under 35 U.S.C. 154(b) by 0 days.

(21) Appl. No.: 09/337,287

(22) Filed: Jun. 21, 1999

Related U.S. Application Data

(60) Provisional application No. 60/090,629, filed on Jun. 25, 1998, provisional application No. 60/090,638, filed on Jun. 25, 1998, provisional application No. 60/090,673, filed on Jun. 25, 1998, and provisional application No. 60/091,054, filed on Jun. 29, 1998.

(51) Int. Cl.$^7$ .................................................. G10N 29/18
(52) U.S. Cl. ................................ 73/597; 73/639; 73/159
(58) Field of Search ........................... 73/597, 598, 639, 73/602, 627, 628, 635, 644, 1.82, 1.84, 159

(56) References Cited

U.S. PATENT DOCUMENTS

| | | | |
|---|---|---|---|
| 4,291,577 | * | 9/1981 | Baum et al. ............................. 73/639 |
| 4,688,423 | * | 8/1987 | Orkosalo ................................. 73/598 |
| 4,735,087 | * | 4/1988 | Hourani et al. ......................... 73/639 |
| 4,750,368 | * | 6/1988 | Shearer et al. ......................... 73/600 |
| 5,048,340 | * | 9/1991 | Thompson et al. .................... 73/597 |
| 5,398,538 | * | 3/1995 | Williams et al. ....................... 73/597 |
| 5,493,910 | * | 2/1996 | Hall et al. ............................... 73/597 |
| 5,493,911 | * | 2/1996 | Hall et al. ............................... 73/597 |
| 5,780,744 | * | 7/1998 | Hall et al. ............................... 73/597 |

* cited by examiner

*Primary Examiner*—Helen Kwok
(74) *Attorney, Agent, or Firm*—Fitch, Even, Tabin & Flannery

(57) ABSTRACT

A method and apparatus for determining the caliper and/or the ultrasonic transit time through the thickness direction of a moving web of material using ultrasonic pulses generated by a rotatable wheel ultrasound apparatus. The apparatus includes a first liquid-filled tire and either a second liquid-filled tire forming a nip or a rotatable cylinder that supports a thin moving web of material such as a moving web of paper and forms a nip with the first liquid-filled tire. The components of ultrasonic transit time through the tires and fluid held within the tires may be resolved and separately employed to determine the separate contributions of the two tire thicknesses and the two fluid paths to the total path length that lies between two ultrasonic transducer surfaces contained within the tires in support of caliper measurements. The present invention provides the benefit of obtaining a transit time and caliper measurement at any point in time as a specimen passes through the nip of rotating tires and eliminates inaccuracies arising from nonuniform tire circumferential thickness by accurately retaining point-to-point specimen transit time and caliper variation information, rather than an average obtained through one or more tire rotations. Morever, ultrasonic transit time through the thickness direction of a moving web may be determined independent of small variations in the wheel axle spacing, tire thickness, and liquid and tire temperatures.

16 Claims, 15 Drawing Sheets

Pulse set 1

*Pulse set 2*

Pulse set 1

Pulse set 2

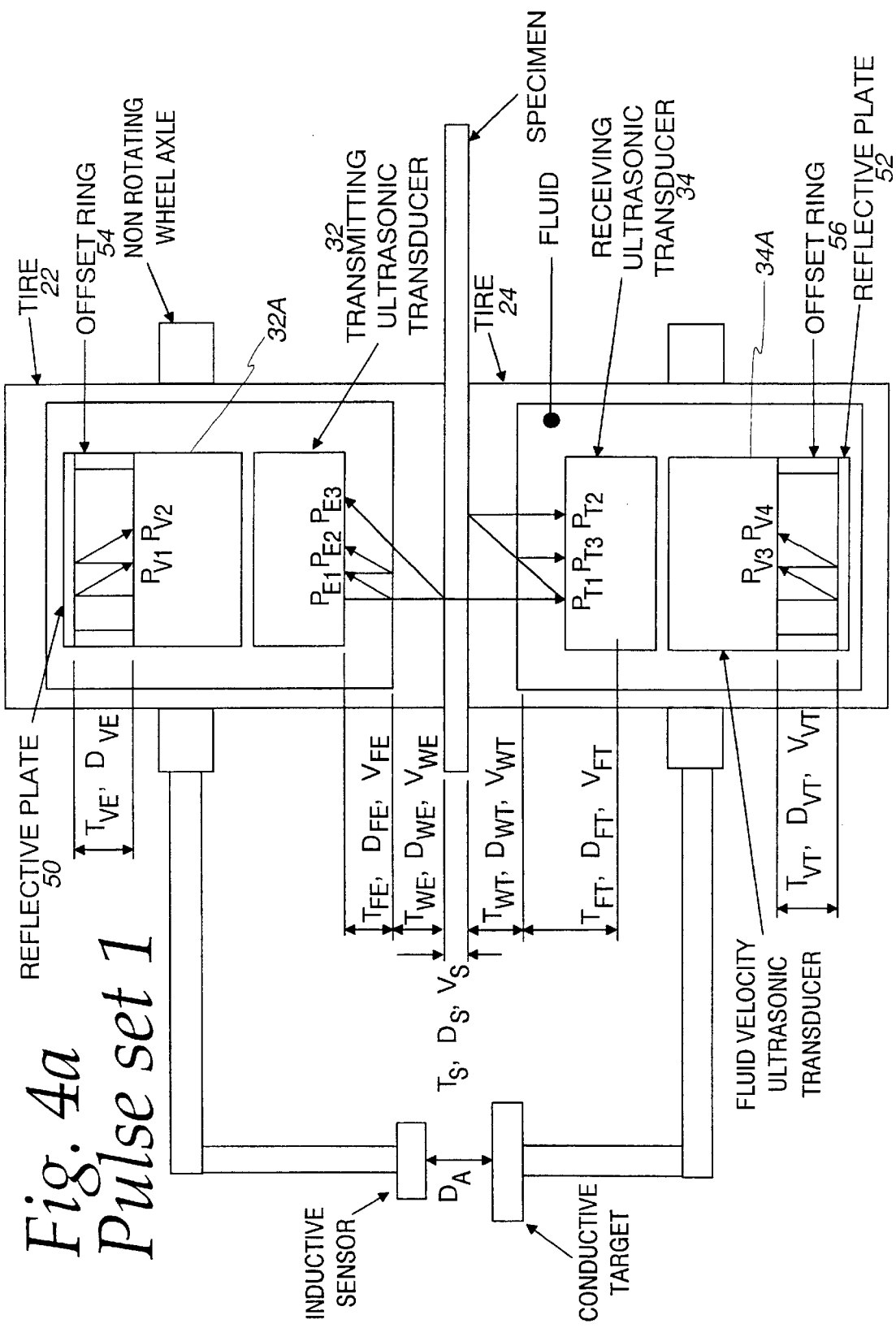

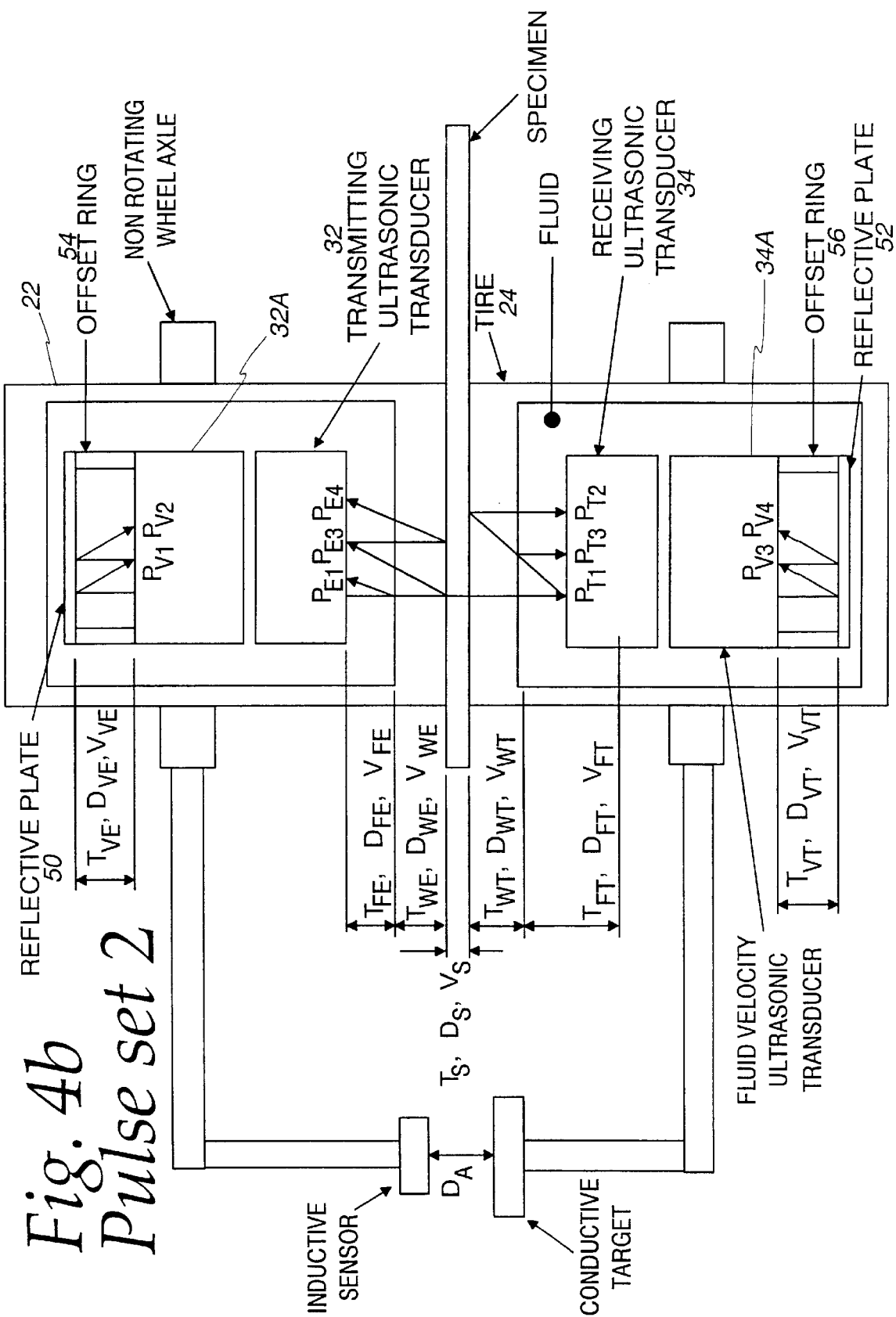

Pulse set 1

Pulse set 2

Pulse set 1

Pulse set 2

METHOD AND APPARATUS FOR ULTRASONIC CHARACTERIZATION THROUGH THE THICKNESS DIRECTION OF A MOVING WEB

CROSS REFERENCE TO RELATED APPLICATIONS

Priority is claimed from co-pending U.S. application Ser. No. 60/090,629, filed Jun. 25, 1998, from co-pending U.S. application Ser. No. 60/090,638, filed Jun. 25, 1998, from co-pending U.S. application Ser. No. 60/090,673, filed Jun. 25, 1998 and from co-pending U.S. application Ser. No. 60/091,054, filed Jun. 29, 1998.

GOVERNMENT RIGHTS

The government of the United States has rights in this invention pursuant to Contract No. DE-FC02-95CE41156 awarded by the U.S. Department of Energy.

FIELD OF THE INVENTION

The present invention generally relates to a method and apparatus for using ultrasonic pulses in a rotating wheel ultrasonic measurement system, and more particularly, the present invention relates to a system for determining several ultrasonic transit times for ultrasonic characterization, that is, ultrasonic transit time and velocity through and thickness of specimen areas of a moving web of material through the thickness direction.

BACKGROUND OF THE INVENTION

Web-like materials, such as paper, paperboard, and the like typically are required to meet particular mechanical property specifications. Normal quality control techniques require testing of the web-like materials to ensure that the web uniformly meets the desired mechanical property specifications.

Destructive-type tests are known for measuring mechanical properties of such web-like materials. Such destructive-type tests are normally conducted off-line on representative samples of the web. There are various problems with such off-line destructive-type testing. For example, such testing is relatively time-consuming and requires production to be sampled periodically when product is received from the machine. In addition, due to the destructiveness of such testing, it is normally performed on representative samples of the web, which may be taken, for example, every several thousand square feet of material. In such a situation, a substantial amount of waste is incurred if the web-like material is found to fail the test.

To solve the problems associated with such destructive-type test measurements of mechanical properties of web-like materials, ultrasonic testing techniques have been developed. Such testing is performed on-line and thus is relatively quicker than off-line destructive-type testing. In addition, ultrasonic testing provides relatively continuous indication of various mechanical properties of the web-like material to assure virtually uniform quality of the product while minimizing waste.

In known ultrasonic systems for testing various mechanical properties, two ultrasonic transducers are provided. The ultrasonic transducers are generally disposed on opposing sides of the web to allow ultrasonic signals to be transmitted in a direction generally normal to the plane of the web. In such a system, one transducer acts as a transmitter while the other transducer as a receiver. The time of flight of an ultrasonic signal through the thickness of the web and the thickness of the web itself are obtained to determine various mechanical properties of the web. In particular, the time of flight of the ultrasonic signal through the thickness of the web is determined by measuring the time of flight of the ultrasonic signal between the transducers during a condition when there is no web or sample present and then measuring the time of flight of the ultrasonic signal during a condition when a web is disposed between the transducers. Consequently, the difference in the times of flight during the two conditions is representative of the time of flight of the ultrasonic signal through the web.

A method and apparatus disclosed in U.S. Pat. No. 5,493,911 ("'911") only provide what is effectively an average ultrasonic measurement over one or more tire circumference lengths. The '911 system requires an electronic rotational synchronization circuit to ensure that each measurement actually represents an average of measurements through one or more rotations of the pair of rotatable tires. The averaging and the rotational synchronization are necessary because this method is unable to account for variations in tire thickness along the circumference of the tire which lead directly to errors in specimen thickness and ultrasonic transit time measurements. This averaging process effectively averages the tire thickness variation out of the measurements. Consequently, the measurements are then distributed over sizable lengths along the specimen, thereby foregoing any chance of maintaining localized measurements of small specimen areas of the sheet.

Also, the nature of the use of the off-sheet calibration in the '911 system is limited due to the assumption that the two tires remain in the same relative rotational synchronization during on-sheet specimen measurements and off-sheet calibration. This assumption implies that the tires would need to have the same circumference, which is a condition that generally is difficult to achieve. As the two tires rotate slowly out of relative synchronization, the quality of the off-sheet calibration tends to degrade.

Prior systems also suffer from the problem that while wheel rotation variance can be partially alleviated by averaging, no instantaneous determination can be made. This limitation creates uncertainty in determining whether the wheel rotation variation has been taken into account when determining a transit time or caliper measurement for a sheet. This uncertainty is due in part to the inability to directly determine the initial and ongoing characteristics associated with the two wheel system—for example, the speed of propagation of ultrasonic pulses through the liquid.

In these systems, a solid delay line is used to roughly measure the speed of propagation through the liquid. The time of transit of ultrasound through the delay line is affected to some extent due to temperature changes of the liquid. These systems, while better than not having any compensation, are not completely error free. For instance, the temperature of the solid delay line naturally tends to lag the temperature of the liquid when the temperature of the liquid is changing. Without knowing the speed of propagation through the liquid to a high degree of certainty, it is difficult to infer the exact length of the fluid path within the tires from pulse reflection times within the solid delay line, and in turn, make accurate measurements of the transit time through the specimen or the specimen thickness (caliper).

What is needed then is a system for accurately and rapidly determining the transit times through all of the media through which the ultrasonic pulses are being propagated so that the transit time through the specimen can be accurately determined. Also, what is needed is a system for accurately and rapidly determining the path lengths through all of the media through which the ultrasonic pulses are being propagated so that accurate determinations of specimen thickness can be made. Finally, what is needed is a system for determining the transit time of ultrasound through specimens that is independent of the velocity of ultrasound through the fluid.

SUMMARY OF THE INVENTION

The present invention solves the above-desired needs by providing a method and apparatus for the ultrasonic measurement of the ultrasonic transit time through the thickness of moving webs of materials. The present invention provides the benefit of obtaining a transit time and caliper measurement at any point in time as a specimen passes through the nip of rotating tires. An exemplary embodiment eliminates inaccuracies arising from nonuniform tire circumferential thickness. Specifically, this embodiment is insensitive to the variations in tire circumferential thickness because the components of ultrasonic transit time through the tires and fluid held within the tires ($T_{fe}$, $T_{we}$, $T_{wr}$ and $T_{fr}$) may be resolved and separately employed to determine the separate contributions of the two tire thicknesses and the two fluid paths to the total path length that lies between the two ultrasonic transducer surfaces in support of caliper measurements. This total path length also includes the thickness of the portion of the specimen currently in the nip between the tires. More importantly, the exemplary embodiment accurately retains point-to-point specimen transit time and caliper variation information, rather than an average obtained through one or more tire rotations. Thus, the present invention provides an ultrasonically-measured transit time and caliper through a portion of the specimen, where the area of the portion is equal to the cross-sectional area of the propagating ultrasonic wave front through the point of nip contact between the tires. Morever, ultrasonic transit time through the thickness direction of a moving web may be determined independent of small variations in the wheel axle spacing, tire thickness, and liquid and tire temperatures.

Another embodiment of the present invention employs a pair of rotatable wheels or tires that are filled with liquid. Each wheel has a transducer positioned therein. In support of the thickness measurement, the transducers each have an associated liquid pulse propagation speed determining cell. The cell comprises an orifice plate for providing a reflective surface and has a bore formed therein. A portion of the ultrasonic pulse emitted by the transducer strikes the orifice plate and is reflected back to the transducer. The region between the transducer and the orifice plate is filled with the same liquid as the tire. The liquid within the tire is free-flowing and well-mixed via tire rotation. The tire rotation also creates a homogenous temperature throughout the fluid contained by the tire. The speed of propagation of ultrasonic pulses moving through any portion of the liquid within the tire at that instant can be determined based on the roundtrip transit time of ultrasound through the cell and the known path length of the fluid inside the cell. In addition, a portion of the same pulse exits through the bore of the orifice plate, travels through the fluid lying between the transducer surface and the interior surface of the tire and strikes the interior surface of the tire wall at the fluid/tire boundary. Due to the selected tire material having a high acoustic impedance mismatch relative to the fluid filling the wheels, a relatively large portion of the ultrasonic energy reaching the boundary will not pass through the tire, but will reflect off of the fluid/tire boundary and travel back through the fluid path to the transducer surface, where a portion of that energy will be converted into an electrical signal by the transducer. This reflected energy constitutes an additional ultrasonic pulse, which may be employed in subsequent specimen thickness and transit time measurements.

The ultrasonic energy pulses are converted by the two transducers into two electrical signals, which are digitized into two concurrent arrays of sampled signal amplitudes. The two arrays are employed by a computer in the determination of 1) the transit time and velocity of ultrasound within the measurement cell, 2) the transit time through the longer fluid path between the transducer surface and the fluid/tire boundary, and therefore, 3) the path length of the fluid filling the space between the transducer surface and the inner tire wall. From the two arrays, additional determinations of the thickness of the two tire walls can be made, as well as the fluid path length of the fluid within the opposite wheel. Knowing the sum of these four distances relative to what they would be with no specimen in the nip allows a measurement of specimen thickness (caliper) to be determined. Specimen thickness is determined from the total of the two fluid path lengths that have been displaced by the presence of the specimen.

In an alternative embodiment of the system, separate transducers are used for transmitting pulses through the specimen and for calibrating the velocity of ultrasound through the fluid. The fluid velocity measurement cells rely on reflection, as in the previous embodiment, to provide a round trip pulse return path. However, in this embodiment, 1) there is no bore in the reflector plate, 2) the reflection is total, rather than partial, and 3) there is no reflector plate placed in the propagation path of the ultrasound that is transmitted through the specimen by the transmitting transducer. From the fluid velocity information and based on additional pulse return times, as set forth above and as described below, the caliper of a specimen can be accurately determined.

It may also be appreciated that a determination can be made of the wall thickness of the tires by inference from the time of pulse transit through the wall thickness.

When the tires are rotating with sufficient speed, a microgap of air forms between the tires. While this microgap of air does not result in a substantial pulse delay, it does provide an acoustic impedance mismatch at the outer tire surfaces where the tires meet at a nip. Normally, such an impedance mismatch would not be present when the tires are rotating slowly with no specimen present, where there is no air gap and the tires are closely coupled acoustically. If the instrument is intended to be used at low speeds, then one tire material may be chosen to differ in acoustic impedance relative to the acoustic impedance of the other tire material to provide a built-in impedance mismatch at the nip boundary. In general, the larger the acoustic impedance mismatch at the nip, the larger the relative amplitude will be of ultrasonic energy pulses reflecting back from the nip. These pulses are useful in the determination of the transit time of ultrasound through the tire thickness and through the ultrasonic propagation path through the fluid in line with the transducer surfaces and the nip.

In another alternative embodiment, a single fluid-filled wheel having a transducer therein is used in association with a rotatable conductive cylinder carrying a specimen. The rotatable conductive cylinder is passive in that it does not contain any transducers, and is conductive in that it provides a return signal to an electrically inductive sensor associated with it. The electrically inductive sensor is indicative of the wheel axle to cylinder surface distance between the fluid-filled wheel and the rotating cylinder. The distance between the transducer surface and the cylinder surface is equal to that measured distance minus the constant distance between the wheel axle and the transducer surface. This embodiment can be used for determining thickness (caliper) measurement of a sheet and uses a fluid-filled wheel having a transducer associated with it in the manner set forth above. This embodiment is not intended for the measurement of the transit time of ultrasound through the specimen, because it is not expected that an ultrasonic signal will transit the specimen thickness twice and reflect from the specimen/cylinder boundary with sufficient amplitude to be useful. In this embodiment, the nip with no specimen present is now constituted by the boundary between the outer tire surface and the surface of the cylinder.

A principal aspect of the present invention is to provide an apparatus and a method for accurately determining characteristics of the measurement apparatus itself from which are derived improved transit time and caliper measurements of a moving web. The accuracy of these measurements is independent at any given instant in time of ambient environmental temperature changes. The accuracy of measurements is also independent of the precise relative separation distance between the axles of the two wheels, and therefore, independent of the distance between the two transducer surfaces within the wheels. This independence enables the apparatus to be mounted on web scanning platforms, wherein the distance between the axles of the two wheels is not necessarily a constant, with no substantial loss in the accuracy of specimen transit time and/or thickness measurements.

BRIEF DESCRIPTION OF THE DRAWINGS

FIG. 4a is a schematic of another alternative embodiment of the present invention having liquid pulse propagation speed determining cells that are separate from the specimen transmission transducers within the wheels suitable for measuring both specimen thickness (caliper) and ultrasonic transit time;

FIG. 4b is a schematic of the embodiment of FIG. 4a of the present invention showing details of an alternative pulse set for measuring specimen thickness (caliper) and ultrasonic transit time;

DETAILED DESCRIPTION OF THE PREFERRED EMBODIMENTS

Figure 1:
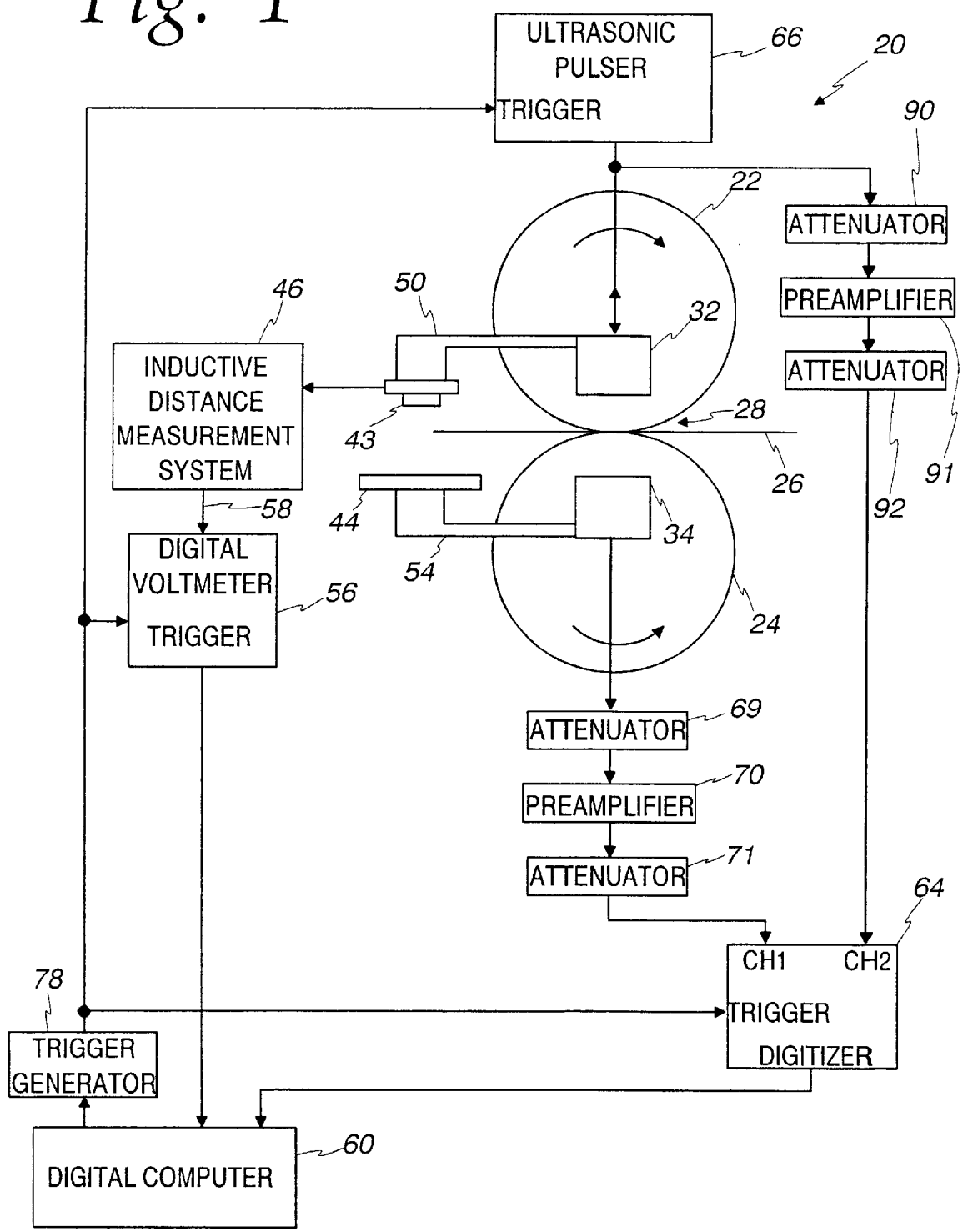
FIG. 1 is a block diagram of an apparatus for determining the transit time and the caliper through the thickness direction of a thin moving web embodying the present invention.

Referring now to the drawings and especially to FIG. 1, a system embodying the present invention is shown therein and generally identified by reference numeral 20. The system 20 includes a pair of fluid-filled rotatable elements, which in some embodiments are fluid-filled rotatable wheels having tires and in other embodiments are a fluid-filled wheel and a rotatable conductive cylinder. In particular, a top wheel 22 is shown and a bottom rotating element 24, which may be a bottom wheel 24 or a bottom rotating cylinder. The liquid-filled wheels 22 and 24 are disposed about mutually parallel axes (not shown). The distance between them is adjusted so that the liquid-filled wheels 22 and 24 are in contact with each other or with a sample when there is a sample present. During operation, web-like materials or samples 26, such as paper, paperboard and other such products, are fed into a nip 28 defined by the interface between the liquid-filled wheels 22 and 24, as generally shown in FIG. 1.

As referred to herein, the terms "wheel" and "tire" are used interchangeably, except as otherwise specified. Also, as referred to herein, the terms "fluid" and "liquid" are used interchangeably.

The transit times of certain ultrasonic signals between the liquid-filled wheels 22 and 24, both with and without a sample present, are used to determine the transit time of an ultrasonic pulse through and the thickness of the web-like material 26, also referred to herein as a sample or specimen. These determinations are in turn used to determine the velocity of ultrasound through and various mechanical properties of the web-like material 26 in a nondestructive and nonobtrusive manner, while the web-like material is moving along a production line. By providing a continuous and nondestructive method for determining the transit time and, in turn, various mechanical properties of web-like material 26, quality control of the web-like material 26 is thus greatly improved, while at the same time, the cost of producing a high quality web is significantly decreased.

Errors in known ultrasonic testing systems affect the accuracy of the transit time and specimen thickness (caliper) measurements. These errors also may affect the accuracy of mechanical properties that are based on the transit time measurements. Error sources may include variations in the transducer wheel thickness and changes in the velocities of ultrasound through the liquid and the tire thickness, which are dependent on the temperature of the liquid and the tires.

More specifically, it is known that the time of flight of an ultrasonic pulse varies as a function of the particular medium through which the pulse propagates. Thus, the time of flight of an ultrasonic pulse in a liquid will be different from the time of flight of such an ultrasonic pulse through other media, for example, the tire walls of the rotating wheels. Thus, a variance in the tire wall thickness of the wheels about their circumference will affect the transit times of ultrasonic pulses throughout their acoustical paths. As such, any web mechanical property determinations based upon such ultrasonic measurements may include errors due to variation in the wall thickness. To compensate for this variation, the transit times and propagation speeds are determined through separate determination of the path lengths of the liquid within the wheels and the tire walls.

The system 20 also includes a pair of immersion-type ultrasonic transducers 32 and 34 disposed within the liquid-filled wheels 22 and 24, respectively. The ultrasonic transducers 32 and 34 may be formed from materials such as ceramic or plastic piezoelectric materials. Such immersion transducers may be purchased from either Panametrics Corporation of Waltham, Mass. or Dapco Industries of Richfield, Conn. The liquid-filled wheels 22 and 24 are typically seven inches in diameter and 3/8 inch thick, for example, as supplied by Dapco Industries, and are typically composed of silicone rubber. However, it will be appreciated that any tire material composed of an elastomer, such as silicon rubber or polyurethrane, may be used as long as the material can tolerate temperatures of up to about 250° C., is chemically inert, and is wear resistant. In this case, the silicone rubber provides a high impedance mismatch between the water/propylene glycol liquid mixture within the wheels and the tire walls. It is further appreciated by those skilled in the art that the present invention is not limited to the above-described liquid mixture, but may use any liquid that is chemically and thermally stable and has an acoustic impedance appropriate for the various applications. Another example of such a liquid may include silicon oil. The transducers 32 and 34 are rigidly affixed to the respective axes about which the wheels 22 and 24 rotate, respectively. The wheels 22 and 24 are positioned such that their respective axes of rotation are parallel and spaced apart so the wheels 22 and 24 touch when there is no specimen 26.

As previously mentioned, relatively small variations in the separation distance between the ultrasonic transducers 32 and 34 may cause errors in transit time measurements. Thus, an inductive distance measurement system 46 continuously monitors the distance between the transducers 32 and 34 to provide immediate correction for variations in transducer separation distance, thereby increasing the accuracy of the calculated velocities.

The inductive distance measurement system 46, for example, a Kaman Instrumentation Corporation Model No. KD-2300-6C, by Kaman Instrumentation Corporation of Colorado Springs, Colo., includes a conductive metal target 44 attached to a support 54 connected to the lower wheel 24. An inductive type sensor 43 is attached to a support 50, which is in turn connected to the upper wheel 22. The inductive measurement system 46 provides a voltage output proportional to the separation distance between the conductive target 44 and the inductive sensor 43, and hence, the transducers 32 and 34 plus some constant distance. A detailed description of such a inductive measurement system 46 is provided in Detail Part 1, *The Workbook Applications Information,* pp. 5–13, by Kaman Instrument Corporation. It will be appreciated by one skilled in the art that the sensor 43 and target 44 may be placed on the lower and upper wheels 24 and 22, respectively, as opposed to the previously described configuration.

As shown in FIG. 1, the output voltage of the inductive measurement system 46 is applied through an electric cable 58 to a digital voltmeter 56, for example, a National Instruments ATMIO-16E-1 analog-to-digital converter board, by National Instruments of Austin, Tex. The digital voltmeter 56 is connected to a digital computer 60. The digital computer 60 is preferably a personal computer based upon an Intel 80486, Pentium microprocessor or better, by Intel Corporation of Santa Clara, Calif.

A high speed digitizer 64 is also included in the system 20 and connected via an external interface to the digital computer 60. The digitizer 64 comprises two-channel or four-channel analog-to-digital converters, each of which is capable of running at a sampling rate of 50 MHz. The channels of the digitizer 64 convert the signals of interest to digital values for transmission to the digital computer 60. In particular, the digitizer 64 may have either two channels or four channels varying according to the different embodiments of the present invention. The system 20 is configured for a two-transducer system such that transmitted signals are applied to channel 1 and reflected or echoed signals are applied to channel 2.

The analog-to-digital conversion process in the digitizer 64 is initiated by an external trigger produced by a trigger generator 78, which is connected to the digitizer 64. The trigger generator 78, which is also connected to an ultrasonic pulser 66, triggers the pulser 66. The pulser 66, for example, a Model No. 5055PR manufactured by Panametrics of Waltham, Mass., is adapted to generate predetermined electrical spikes or pulses which, when applied to a heavily damped ultrasonic transducer such as the ultrasonic transducer 32, are converted to approximately two cycles of 1 MHz ultrasonic waves.

The transmitted pulses are applied to the digitizer 64 by way of an ultrasonic pulse preamplifier 70. The echo pulses are similarly applied to the digitizer 64 by way of an ultrasonic pulse preamplifier 91. The ultrasonic pulse preamplifiers 91 and 70 may be, for example, a Model 5662 manufactured by Panametrics. The external trigger input of the digitizer 64 is under the control of the trigger generator 78. By connecting the external trigger of the digitizer 64 to the trigger signal generated by the trigger generator 68, the digitizer 64 is triggered to begin digitizing at the same instant that the ultrasonic pulser 66 is triggered to produce an electrical pulse. This pulse causes the ultrasonic transducer 32 to emit a highly damped ultrasonic wave which propagates away from the surface of the transducer 32 through the nip 28 between the wheels 22 and 24 and to the transducer 34.

In one embodiment, variable attenuators 69 and 71 surround the preamplifier 70 for conditioning signals from the transducer 34 prior to digitization. Likewise, variable attenuators 90 and 92 surrounding the preamplifier 91 perform the same function for echo signals from the transducer 32.

Figure 2A:
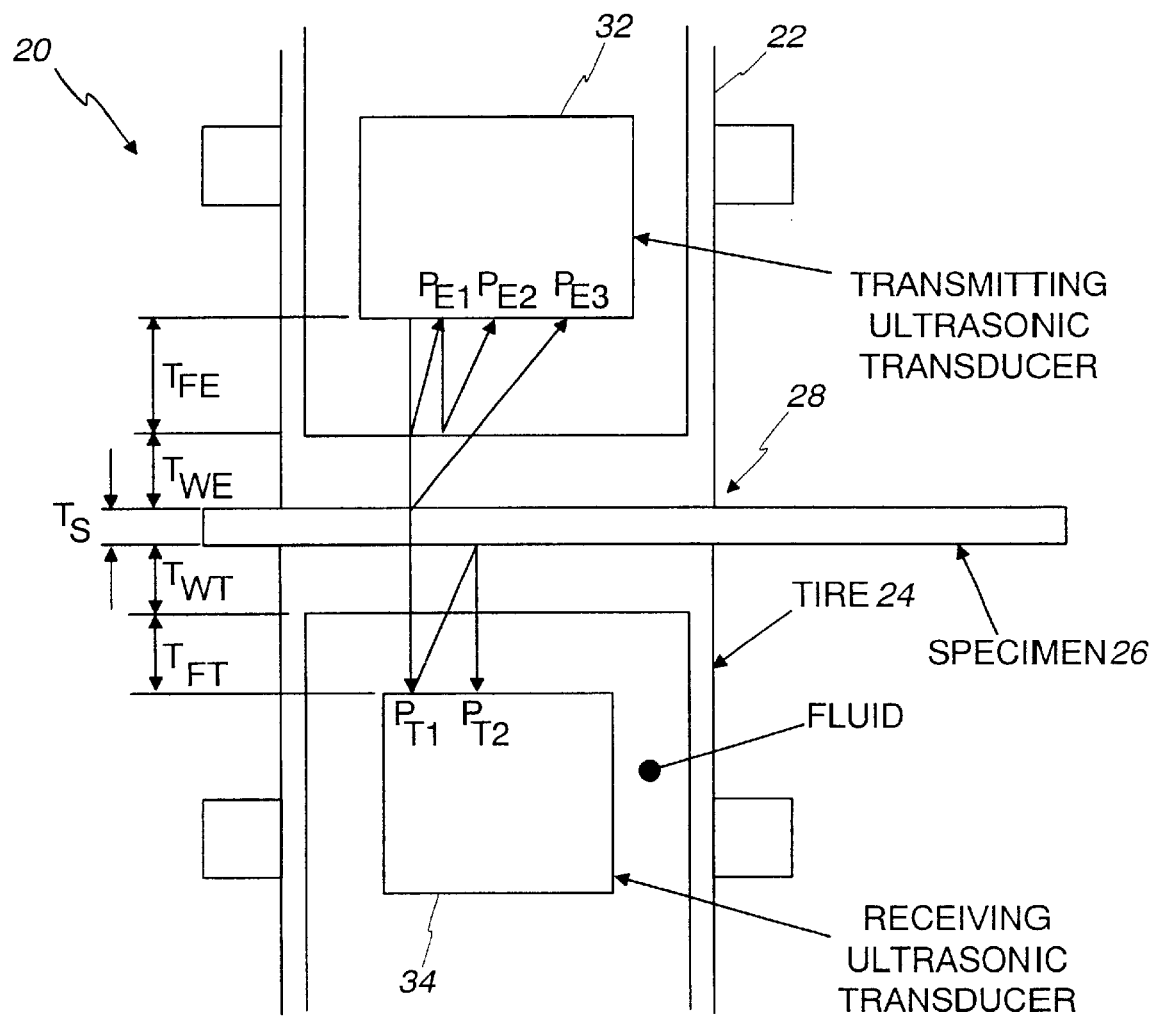
FIG. 2a is a schematic of a portion of the apparatus shown in FIG. 1 showing portions of the rotatable wheels together with their associated transducers illustrating ultrasonic pulse propagation paths suitable for measuring the transit time of ultrasound through the thickness of the specimen.

Every measurement begins with the emission of a short duration, highly-damped ultrasonic pulse from the transmitting ultrasonic transducer 32. After emitting an ultrasonic pulse, the transducer 32 then receives ultrasonic pulse echoes arising from the original emission. Ultrasonic energy propagates away from the surface of the transducer 32 in substantially a plane wave through the liquid within which the transducer 32 is immersed until the ultrasonic pulse wave front reaches the boundary between the fluid and the inside of the corresponding wheel 22. At the liquid-tire wall boundary, a portion of the energy (pulse wave) is reflected back from the boundary of the wheel 22 and the rest of the energy (pulse wave) propagates through the boundary into the wheel or tire wall thickness as shown in FIG. 2a, for example. Every boundary between pairs of adjacent media typically produces a transmitted and a reflected pulse in this way. This sequence of events ultimately produces a train of ultrasonic pulses that are spaced apart and arrive over time at both the emitting transducer 32, now acting as an echo receiver, and the receiving transducer 34.

Among the many "child" pulses arising from the original emission, several pulses within the pulse trains are useful for the measurement of ultrasonic transit time through the specimen and the measurement of the thickness (caliper) of the specimen.

Now turning to FIGS. 2a–12, systems and methods for determining the ultrasonic transit time and the caliper of a specimen are shown.

Measurement of Ultrasonic Transit Time

Figure 2B:
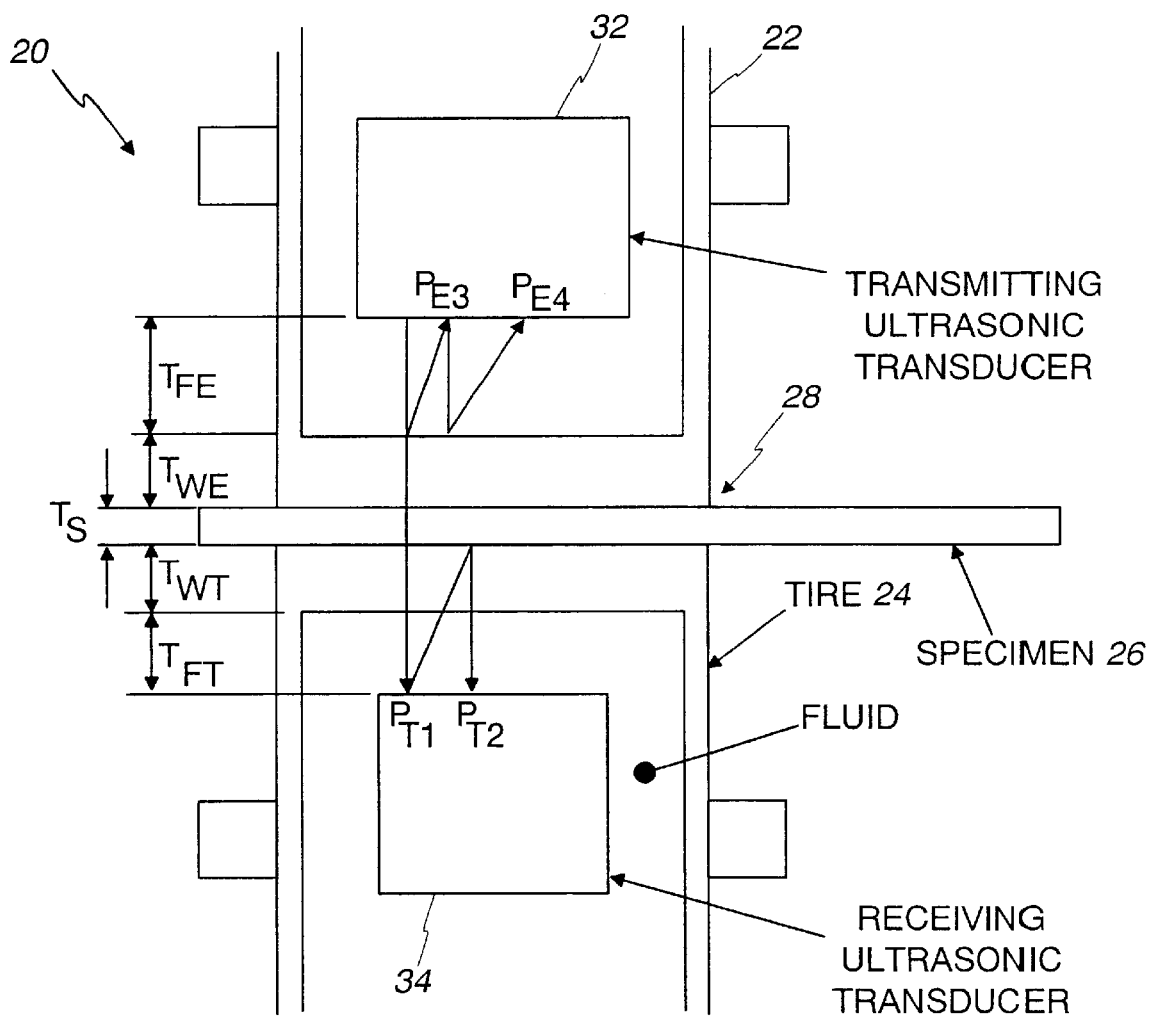
FIG. 2b is a schematic of portions of the rotatable wheels together with their associated transducers shown in FIG. 2a illustrating alternative ultrasonic pulse propagation paths suitable for measuring the transit time of ultrasound through the thickness of the specimen.

FIGS. 2a and 2b illustrate one embodiment of the present invention for measuring transit time in a specimen. As previously mentioned, to determine the transit time for a specimen, a set of pulses is selected from a pulse train. Referring to FIG. 2a, the pulses of interest are labeled $P_{e1}$, $P_{e2}$, $P_{e3}$, $P_{t1}$ and $P_{t2}$.

The selected pulses corresponding to a selected pulse set must be separated in time from other pulses arriving at either transducer surface. To do so, the path lengths of the selected pulses through the media are chosen such that the selected pulses are clearly resolved in time from each other and from the pulses that were not selected. The relative time offset between pairs of pulses in a selected pulse set may then be determined.

The relative time offset between a pair of selected pulses may be determined numerically via a cross-correlation integral represented as $CR(P_a, P_b)$. The calculation of transit time ($T_s$) through the specimen via the pulse set illustrated in FIG. 2a may be determined by equations (1)–(7) as set forth below:

$$CR(P_{e1}, P_{e2}) = (4 * T_{fe}) - (2 * T_{fe}) \quad (1)$$
$$= 2 * T_{fe}$$

$$CR(P_{e1}, P_{e3}) = (2 * T_{fe} + 2 * T_{we}) - (2 * T_{fe}) \quad (2)$$
$$= 2 * T_{we}$$

$$CR(P_{t1}, P_{t2}) = (T_{fe} + T_{we} + T_s + 3 * T_{wt} + 3 * T_{ft}) - \quad (3)$$
$$(T_{fe} + T_{we} + T_s + T_{wt} + T_{ft})$$
$$= 2 * T_{ft} + 2 * T_{wt}$$

-continued
$$CR(P_{e3}, P_{t1}) = (T_{fe} + T_{we} + T_s + T_{wt} + T_{ft}) - (2 * T_{fe} + 2 * T_{we}) \quad (4)$$
$$= T_s + T_{wt} + T_{ft} - T_{fe} - T_{we}$$
$$= T_s + CR(P_{t1}, P_{t2})/2 - CR(P_{e1}, P_{e2})/2 -$$
$$CR(P_{e1}, P_{e3})/2$$

So:

$$T_s = CR(P_{e3},P_{t1}) + CR(P_{e1},P_{e2})/2 + CR(P_{e1},P_{e3})/2 - CR(P_{t1},P_{t2})/2 \quad (5)$$

Alternatively:

$$CR(P_{e1}, P_{t1}) = (T_{fe} + T_{we} + T_s + T_{wt} + T_{ft}) - (2 * T_{fe}) \quad (6)$$
$$= T_s + T_{wt} + T_{ft} - T_{fe} + T_{we}$$
$$= T_s + CR(P_{t1}, P_{t2})/2 - CR(P_{e1}, P_{e2})/2 +$$
$$CR(P_{e1}, P_{e3})/2$$

So:

$$T_s = CR(P_{e1},P_{t1}) + CR(P_{e1},P_{e2})/2 - CR(P_{e1},P_{e3})/2 - CR(P_{t1},P_{t2})/2 \quad (7)$$

In FIG. 2b, an alternative pulse set is selected. The pulses of interest are labeled $P_{e3}$, $P_{e4}$, $P_{t1}$, and $P_{t2}$. The calculation of transit time is even simpler, as only two echo side pulses are needed. The calculation of transit time through the specimen may be determined as set forth below by equations (8)–(11):

$$CR(P_{e3}, P_{e4}) = (4 * T_{fe} + 4 * T_{we}) - (2 * T_{fe} + 2 * T_{we}) \quad (8)$$
$$= 2 * T_{fe} + 2 * T_{we}$$

$$CR(P_{t1}, P_{t2}) = (T_{fe} + T_{we} + T_s + 3 * T_{wt} + 3 * T_{ft}) - \quad (9)$$
$$(T_{fe} + T_{we} + T_s + T_{wt} + T_{ft})$$
$$= 2 * T_{ft} + 2 * T_{wt}$$

$$CR(P_{e3}, P_{t1}) = (T_{fe} + T_{we} + T_s + T_{wt} + T_{ft}) - \quad (10)$$
$$(2 * T_{fe} + 2 * T_{we})$$
$$= T_s + T_{wt} + T_{ft} - T_{fe} - T_{we}$$
$$= T_s + CR(P_{t1}, P_{t2})/2 - CR(P_{e3}, P_{e4})/2$$

So:

$$T_s = CR(P_{e3},P_{t1}) + CR(P_{e3},P_{e4})/2 - CR(P_{t1},P_{t2})/2 \quad (11)$$

It will be appreciated that pulses labeled $P_{e1}$, and $P_{e2}$ (FIG. 2a) represent bounces from a liquid-tire interface within a tire, whereas pulses labeled $P_{e3}$, $P_{e4}$, and $P_{t2}$ (FIG. 2b) represent ultrasonic pulse bounces between the outside surface of a tire and the sample 26 or the outside surface of the other tire when no specimen is present. Based on the foregoing, the selected pulse set shown in FIG. 2b may be preferable to the set shown in FIG. 2a due to one less cross-correlation term needed for the calculation of transit time $T_s$.

For system 20, the calculated value for $T_s$ via either selected pulse set (FIG. 2a or FIG. 2b) is approximately equal to the actual transit time of ultrasound through the specimen 26 at the point of nip contact 28 with the tires 22 and 24. Specifically, the two transducers 32 and 34 and the electronics that amplify the electrical signals generated by the transducers 32 and 34 have slightly different phase response characteristics. These characteristics add a slight constant inaccuracy to the measurement of $T_s$ and must be eliminated.

To eliminate the inaccuracy of the $T_s$ measurement, the specimen is removed from the nip 28 and the measurement of transit time $T_s$ is performed. When there is no specimen present at the nip (off-sheet), the actual transit time through the nip 28 should be exactly zero. However, some small non-zero transit time will generally arise from the calculation of $T_s$, referred to as a residual transit time. Based on the off-sheet measurement, this residual transit time ($T_{s0}$) is directly attributable to the non-identical transducers and electronics phase characteristics mentioned above. If a constant average value for the residual transit time $T_{s0}$ is subtracted from every value of transit time $T_s$ calculated when the specimen 26 is present in the nip 28, then the resulting measurement of transit time $T_s$ will be accurate and free of the transducers and electronics unique phase response characteristics.

During the off-sheet calculation of the residual transit time $T_{s0}$, very little energy is reflected back from the nip 28 due to the very low acoustic impedance mismatch of the tires. This result is especially true when the tires 22 and 24 are not moving or are turning at a relatively slow rotation rate. Also, if the materials for both tires 22 and 24 are identical, the acoustic impedance of the tires will be identical. Thus, for example, the double nip reflected pulse $P_{e4}$ illustrated in FIG. 2b will be very small and will generally have a very low signal-to-noise ratio under those conditions.

For slowly rotating tires with no specimen 26 present, the measurement pulse set shown in FIG. 2a is generally preferable since no second reflection from the nip 28 is involved. If the tires 22 and 24 are moving at a relatively high rotation rate, with no specimen 26 present, then a microscopic air gap will be entrained in the nip 28 between the tire surfaces. This microscopic air gap is sufficient to produce a substantial acoustic boundary that yields larger reflections back from the nip 28 resulting in larger pulse amplitudes $P_{e3}$, and $P_{e4}$, and $P_{f2}$. Yet, the gap is thin enough to contribute only a negligible ultrasonic transit time component to the residual transit time $T_{s0}$. When a specimen is present in the nip 28, regardless of the tire rotation rate, either selected pulse set (FIG. 2a or FIG. 2b) is generally effective in determining transit time. A primary reason is the acoustic impedance mismatch between the tire material and the specimen 26 is generally quite large, thereby producing strong nip reflected pulses from both sides of the specimen.

For the selected pulse set in FIG. 2a, the fluid and tire materials should be chosen to have a substantial acoustic impedance mismatch at the liquid-tire boundary. For the selected pulse set in FIG. 2b, since no fluid-tire boundary reflected pulses are employed, the acoustic impedance mismatch at that boundary is generally irrelevant and may be minimized, for example, by using tires which have an acoustic impedance close to that of the fluid that fills them.

The signals from the transmitting transducer 32 and the signals from the receiving transducer 34 may be digitized concurrently by independent analog-to-digital converters, such as the digitizer 64 (FIG. 1), whose conversion cycles are simultaneously initiated by the same conversion clock signal. The conversion rate preferably is greater by a factor of 10 or more than the frequency of the ultrasonic energy emitted from the transmitting transducers 32 and 34 for optimally accurate measurements.

The system 20 (FIG. 1) is considered free-running as transit time or any given caliper measurement can be taken at any instant during passage of the specimen 26 through the nip 28 due to the rotating tires 22 and 24. Electronic rotational synchronization is not required to obtain an average of measurements through one or more rotations of the tires 22 and 24. The method of the present invention accurately retains point-to-point specimen thickness (caliper) and ultrasonic transit time variation information. The present invention does not rely on average values over one or more tire rotations, as do prior systems. Each measurement represents the ultrasonically-measured caliper and/or transit time through a portion of the specimen 26. The specimen portion is the area that is equal to the cross-sectional area of the propagating ultrasonic wave front that passes through the point of nip contact between the tires 22 and 24.

Measurement of Specimen Thickness (Caliper)

Figure 3A:
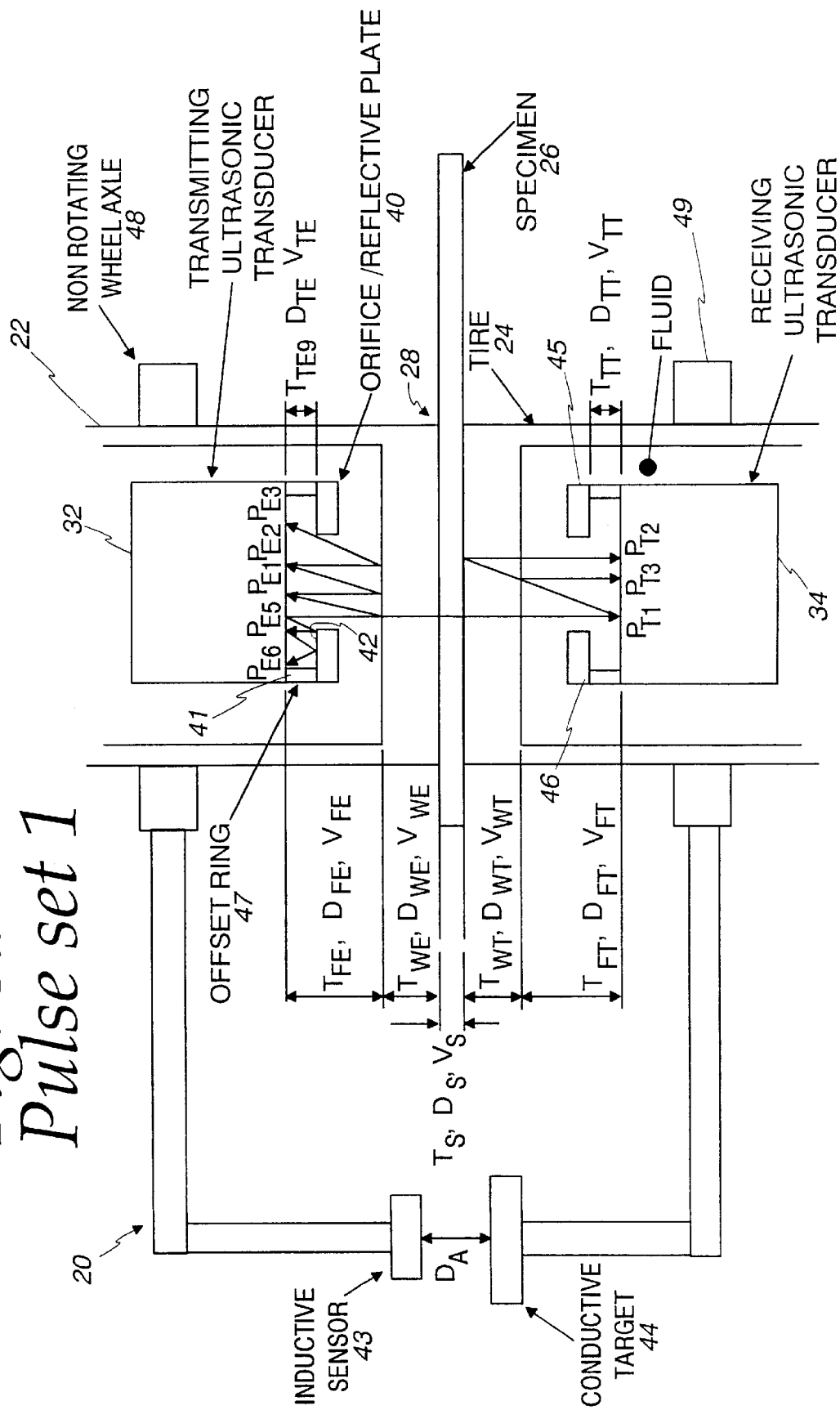
FIG. 3a is a schematic of portions of an alternative embodiment of the present invention showing details of liquid pulse propagation speed measuring cells associated with the transducers, an electrically inductive sensor, and conductive target suitable for measuring specimen thickness (caliper) and transit time.
Figure 3B:
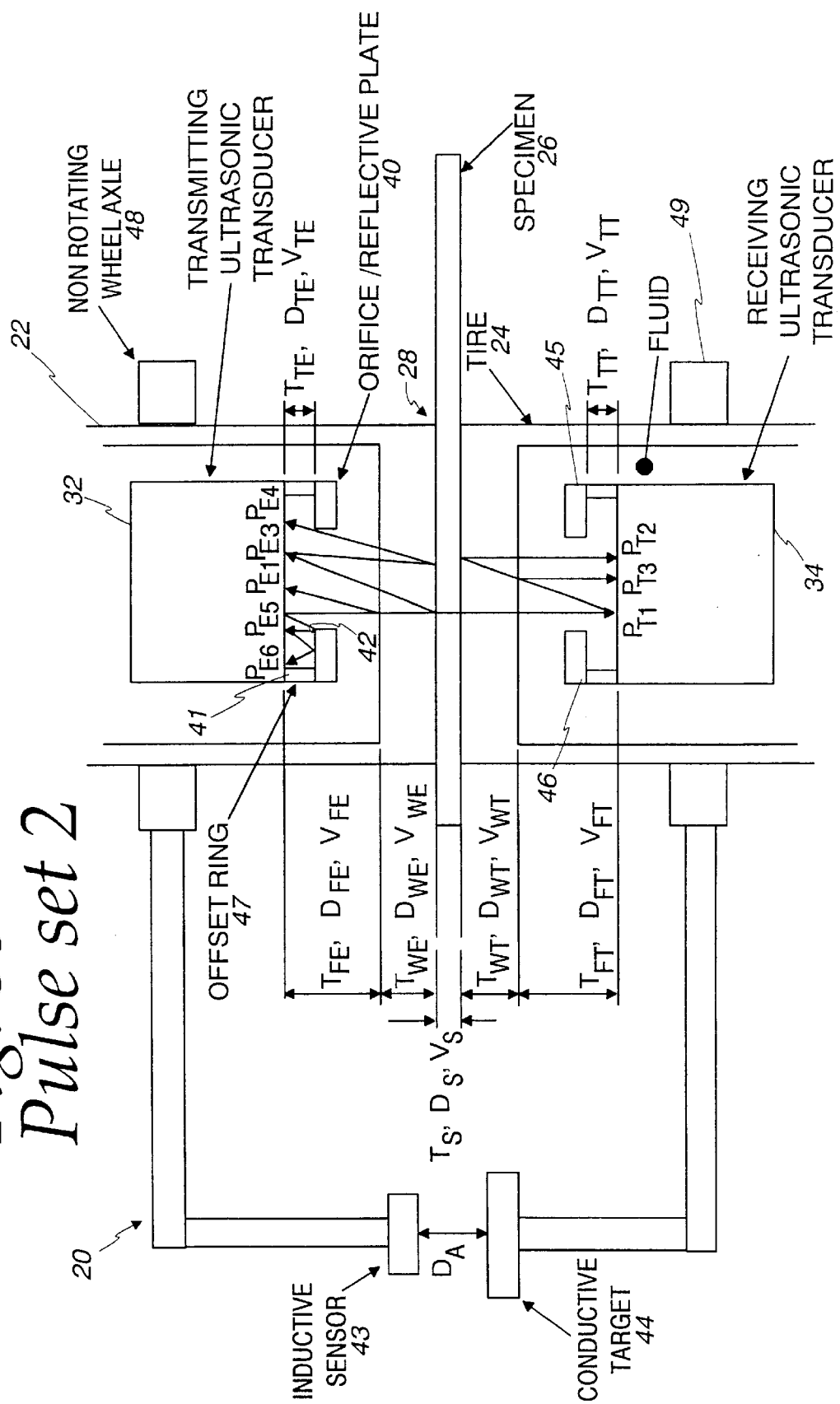
FIG. 3b is a schematic of the apparatus shown in FIG. 3a showing details of an alternative pulse set for measuring specimen thickness (caliper) and transit time.

Referring to FIGS. 3a and 3b, as stated above, every measurement begins with the emission of a short, highly-damped ultrasonic pulse from the transmitting ultrasonic transducer 32. The transducer 32 thereafter receives ultrasonic echoes arising from the initial emission. The substantially planar wave front initially propagates away from the planar transducer surface through the fluid within which the transducer 32 is immersed until the ultrasonic wave front has traveled a distance $D_{te}$ (see FIGS. 3a and 3b).

Referring to FIGS. 3a and 3b, the portion of the area of the advancing wave front inside a radial periphery of the transducer's active surface 41 and outside an outer edge of a bore that has been cut into a reflective plate 40 reflects back toward the transducer 32. The reflective plate 40 is preferably smooth, flat, and oriented exactly parallel to the surface of the transducer 32. Preferably, the reflective plate 40 is also positioned concentrically with the transducer surface 41. Upon reaching the transducer surface 41, some of that energy is absorbed by the transducer 32 and is converted into an electrical signal representative of $P_{e5}$. The energy is reflected back from the transducer surface 41, propagated back to the reflector surface 42, and reflected back by the reflective plate 40. The energy then arrives at the transducer surface 41 and is converted into an electrical signal $P_{e6}$.

The remainder of the initially-emitted ultrasonic wave front, with a beam diameter equal to the bore diameter in the center of the reflective plate 40, is not reflected by the reflective plate, but is transmitted unobstructed through the bore. The remaining ultrasonic energy is partially reflected and partially transmitted through each of the liquid-tire, liquid-transducer and tire-specimen boundaries located between the two transducers 32 and 34 leading respectively to the creation of pulses $P_{e1}$, $P_{e2}$, $P_{e3}$ (FIG. 3a) and $P_{e4}$ (FIG. 3b). Pulses $P_{f1}$, $P_{f2}$, and $P_{f3}$ (FIGS. 3a and 3b) are created in a like manner.

Ultrasonic transit time and caliper measurements require the determination of relative time offsets between pairs of measurement pulses via a cross-correlation integral technique represented as $CR(P_a,P_b)$ similar to the techniques described in connection with determining transit times.

In FIGS. 3a and 3b, the reflective plate bore diameter will determine the relative amplitudes of the pulses $P_{e5}$ and $P_{e6}$ versus that of pulses $P_{e1}$, $P_{e2}$, $P_{e3}$ and $P_{e4}$. The bore size also determines the diameter of the ultrasonic wave front actually passing through the nip 28 between tires 22 and 24 and the specimen 26, and hence, the area of the specimen 26 that is actually being measured. Measurement of specimen features down to the size of fiber flocculation features in paper, for example, is possible with a sufficiently small bore diameter.

In FIGS. 3a and 3b, the method of specimen thickness measurement relies upon the ability to measure the total length of the fluid path ($D_{fe}+D_{ft}$) in a direction orthogonal to the plane of the specimen 26. To do so, it is necessary first to measure a relative separation distance $D_a$ between an inductive proximity sensor 43 and a conductive target 44.

The inductive proximity sensor 43 is rigidly attached to one wheel axle 48, and the conductive target 44 is rigidly attached to the other wheel axle 49. The sensor 43 and target 44 are situated close to each other on either side of the specimen 26. $D_a$ is equal to the distance between the surfaces of the two transducers 32 and 34 plus some constant distance since both the inductive sensor 43, the target 44, and the two transducers 32 and 34 are rigidly attached to their respective wheel axles 48 and 49. If $D_a$ can be assumed to be a constant at all times, then $D_a$ need not be measured at all. The inductively measured distance between the sensor 43 and the target 44 is insensitive to the presence of the nonconductive specimen between them. The constant distance is arbitrary and is eliminated via the application of the off-sheet calibration.

Referring still to FIGS. 3a and 3b, the ultrasonic transit times through the fluid paths, $T_{fe}$ and $T_{ft}$, within the tires are determined for the purpose of ascertaining specimen thickness (caliper). The ultrasonic propagation velocities $V_{te}=V_{fe}$ and $V_{tt}=V_{ft}$ through the two liquid paths must also be known. The speed of pulse propagation through the liquid within the tire 22 is measured by calculating the ultrasonic transit time $T_{te}$ via pulses $P_{e5}$ and $P_{e6}$, which reflect within the known fluid path length $D_{te}$, also referred to as a partial liquid path length.

Knowing $D_{te}$ and the time it takes ultrasound to travel that liquid path length allow the determination of the fluid velocity. It is assumed that the velocity of the fluid measured along the partial liquid path $D_{te}$ is representative of the velocity through the longer liquid path $D_{fe}$, which is the path length of the fluid from the transducer to the inner tire wall. Knowing the velocity of ultrasonic propagation through the liquid in the transmitting tire 22, the calculated ultrasonic transit time $T_{fe}$ through the longer liquid path in combination with the ultrasonic velocity allows the calculation of liquid path length $D_{fe}$.

In FIGS. 3a and 3b, the system 20 provides the ability to determine the liquid pulse propagation speed and the liquid path length within the transmitting tire 22. The reflective plate behaves both as a reflector for producing pulses $P_{e5}$ and $P_{e6}$, and as an orifice that limits the diameter of the planer ultrasonic wave front that actually passes through the specimen 26. An identical reflective plate 45 and offset ring pair 46 are also attached to the receiving transducer 34. However, the receiver reflective plate 45 does not behave as a reflector as does the transmitter reflective plate 40. One reason is the ultrasonic wave front diameter is limited by both plates so that little or no ultrasonic energy enters the volume of liquid enclosed by the receiver reflective plate 45 and the receiving transducer 34. Thus, plate-reflective pulses within the receiving wheel 24 that would be analogous to pulses $P_{e5}$ and $P_{e6}$ are not produced.

In order to measure the liquid path length $D_{ft}$ within the receiving wheel 24, the transmitting and receiving transducers 32 and 34 must be electronically interchanged such that the transmitting transducer 32 now functions as a receiver and the receiving transducer 34 now functions as a transmitter. To do so, turning to FIG. 1, the ultrasonic pulser 66 must be functionally connected to transducer 34 and attenuator 69 and disconnected from transducer 32 and attenuator 90. In this mode, the liquid path length $D_{ft}$ within the receiving tire 24 is calculated in the same manner as $D_{fe}$, described above. In fact, all "e" pulses, transit times, distances and velocities may now be considered as "t" pulses, transit times, distances and velocities and vice versa, with all measurements proceeding in this new configuration according to the same techniques described above.

It is assumed that the speed of propagation of ultrasonic pulses within the liquid, which is generally proportional to the temperature of the liquid within either tire, does not change instantaneously. It is also assumed that a measurement of liquid propagation speed will be accurate for at least a few moments following a speed determination. Thus, the speed of ultrasonic pulse propagation through the liquid within both tires may be known correctly and concurrently, provided the transmitting/receiving mode is toggled often enough. Irrespective of the fact that fluid velocity is actually measured within only one tire at a time, the liquid pulse propagation path lengths $D_{fe}$ and $D_{ft}$ may be measured simultaneously at all times since $T_{fe}$ and $T_{ft}$ may be measured simultaneously in either mode.

The reflective plate 40 is separated from the transducer surface 41 by a fixed distance $D_{te}$ that is determined by the length of the offset ring 47 that is rigidly attached to the transducer surface 41 at one end and to the reflective plate 40 on the other end. Two holes (not shown) may be bored into opposite sides of the circumference of the offset ring to allow free flow of liquid through the gap between the transducer surface 41 and the reflective plate 40. In this way, the temperature of the liquid in the gap, and hence, the ultrasonic velocity through the liquid, is representative of the temperature of the rest of the liquid within the tire 22 or 24 and, in particular, the temperature of the liquid flowing through the longer ultrasonic propagation path.

The reflective plate 40 preferably is made from a material that has a large acoustic impedance mismatch relative to the acoustic impedance of the liquid within which the reflective plate is immersed. This large acoustic impedance mismatch minimizes the proportion of energy transmitted into the orifice or reflective plate 40 itself and maximizes the portion of ultrasonic energy reflected from the reflective plate surface. Generally, any ultrasonic energy transmitted into the reflective plate is internally reflected inside the plate and a portion of the energy leaks out of the plate with each internal reflection. The plate leakage energy is distributed over time and may interfere with the selected pulses for measuring transit time and caliper. This plate leakage energy can be minimized with an appropriate choice of plate material, preferably a high density, high impedance crystalline material, such as sapphire, which will not readily suffer from corrosion.

The tires 22 and 24 within which the ultrasonic transducers 32 and 34 are located, respectively, are generally non-uniform as to their circumferential thickness. For a specimen thickness (caliper) measurement, it is necessary to know the thickness of the walls of both tires 22 and 24 at the point of nip contact 28 ($D_{we},D_{wt}$), both of which generally change cyclically with wheel rotation. To determine these instantaneous tire wall thicknesses, the transit times through both tires at the nip 28 must be measured from which $D_{we}$ and $D_{wt}$ then can be inferred. It is also necessary to have good estimates of the average circumferential thickness of both tires during operation. The average thicknesses are inferred from recent continuously updated tire thickness transit time averages, and depending upon the thermal dimensional characteristics of the chosen tire material, there are at least three ways to infer instantaneous tire thickness from average transit time.

In a first method, if the average tire wall thickness can be expected to increase and decrease with temperature as an arbitrary function of average ultrasonic transit time through the wall thickness, then these two quantities should be measured concurrently at several ambient temperatures throughout the full range of expected ambient temperature conditions during actual operation of the apparatus 20. From this series of measurements a pair of fit functions may be calculated, as set forth in equations (12) and (13):

$$D_{weavg} = f(T_{weavg}) \quad (12)$$

$$D_{wtavg} = f(T_{wtavg}) \quad (13)$$

If the tire material is expected to thermally expand and contract linearly with measured ultrasonic transit time through the expected operational temperature range, then average wall thickness and average transit time should be measured concurrently near the warmest and coolest ambient temperatures to be expected during operation. In this case, the average tire thickness at any given temperature during operation may be inferred from the current average ultrasonic transit time through the wheel thickness during operation according to the two following formulae (14) and (15):

$$D_{weavg} = \frac{D_{weavg\_warm} - D_{weavg\_cool}}{T_{weavg\_warm} - T_{weavg\_cool}} * (T_{weavg} - T_{weavg\_cool}) + D_{weavg\_cool} \quad (14)$$

$$D_{wtavg} = \frac{D_{wtavg\_warm} - D_{wtavg\_cool}}{T_{wtavg\_warm} - T_{wtavg\_cool}} * (T_{wtavg} - T_{wtavg\_cool}) + D_{wtavg\_cool} \quad (15)$$

If the tire material is known to be dimensionally stable through the expected operational temperature range, then $T_{weavg}$ and $T_{wtavg}$ need not be measured at all and the measured values for $D_{weavg}$ and $D_{wtavg}$ may be used as the current average circumferential tire thicknesses at all times during operation.

During operation, $T_{weavg}$ and $T_{wtavg}$, which include measurements of $T_{we}$ and $T_{wt}$ through the several most recent wheel rotations, are continuously determined. $D_{weavg}$ and $D_{wtavg}$ are then inferred by one of the calibration relationships described above.

Next, as part of the current instantaneous caliper measurement, the current unaveraged instantaneous values for $T_{we}$ and $T_{wt}$ are determined. The ratios of the instantaneous values for $T_{we}$ and $T_{wt}$ versus their respective average values are used to determine the ratio of current instantaneous tire thicknesses to their respective averages as set forth in equations (16)–(19):

$$T_{we}/T_{weavg} = D_{we}/D_{weavg} \quad (16)$$

$$T_{wt}/T_{wtavg} = D_{wt}/D_{wtavg} \quad (17)$$

so $$D_{we} = T_{we}/T_{weavg} * D_{weavg} \quad (18)$$

$$D_{wt} = T_{wt}/D_{wtavg} * D_{wtavg} \quad (19)$$

Consequently, the process of caliper measurement proceeds as follows: First, the wheels 22 and 24 are moved off the specimen 26 and the quantities $D_{fe}$, $D_{ft}$, $D_{we}$, $D_{wt}$, $D_{weavg}$, $D_{wtavg}$ and $D_a$ are determined. With the wheels 22 and 24 in contact with no specimen 26 in the nip 28, the current actual caliper is identically zero. A caliper offset $D_{s0}$ is determined as follows:

$$D_{s0} = D_a - (D_{fe} + D_{we} + D_{wt} + D_{ft}) \quad (20)$$

Note that in equation (20), $D_{s0}$ may represent an average of offsheet caliper offsets. Next, the wheels 22 and 24 are moved back onto the specimen 26 and the actual caliper is calculated as shown below in equation (21):

$$D_s = D_a - (D_{fe} + D_{we} + D_{wt} + D_{ft}) - D_{s0}. \quad (21)$$

Equations (22)–(33) are generated to determine the additional variables from the cross-correlation coefficients.

$$CR(P_{e1}, P_{e2}) = (4*T_{fe}) - (2*T_{fe}) \quad (22)$$
$$= 2*T_{fe}$$

$$CR(P_{e1}, P_{e3}) = (2*T_{fe} + 2*T_{we}) - (2*T_{fe}) \quad (23)$$
$$= 2*T_{we}$$

$$CR(P_{e3}, P_{e2}) = (4*T_{fe}) - (2*T_{fe} + 2*T_{we}) \quad (24)$$
$$= 2*T_{fe} - 2*T_{we}$$

$$CR(P_{e5}, P_{e6}) = (4*T_{te}) - (2*T_{te}) \quad (25)$$
$$= 2*T_{te}$$

$$CR(P_{t1}, P_{t2}) = (T_{fe} + T_{we} + T_s + 3*T_{wt} + 3*T_{ft}) - \quad (26)$$
$$(T_{fe} + T_{we} + T_s + T_{wt} + T_{ft})$$
$$= 2*T_{ft} + 2*T_{wt}$$

$$CR(P_{t1}, P_{t3}) = (T_{fe} + T_{we} + T_s + 3*T_{ft}) - \quad (27)$$
$$(T_{fe} + T_{we} + T_s + T_{wt} + T_{ft})$$
$$= 2*T_{ft}$$

$$CR(P_{t3}, P_{t2}) = (T_{fe} + T_{we} + T_s + 3*T_{wt} + 3*T_{ft}) - \quad (28)$$
$$(T_{fe} + T_{we} + T_s + T_{wt} + 3*T_{ft})$$
$$= 2*T_{wt}$$

So:

$$T_{fe} = CR(P_{e1}, P_{e2})/2 = CR(P_{e3}, P_{e2})/2 + CR(P_{e1}, P_{e3})/2 \quad (29)$$

$$T_{we} = CR(P_{e1}, P_{e3})/2 = CR(P_{e1}, P_{e2})/2 - CR(P_{e3}, P_{e2})/2 \quad (30)$$

$$T_{ft} = CR(P_{t1}, P_{t3})/2 = CR(P_{t1}, P_{t2})/2 - CR(P_{t3}, P_{t2})/2 \quad (31)$$

$$T_{wt} = CR(P_{t3}, P_{t2})/2 = CR(P_{t1}, P_{t2})/2 - CR(P_{t1}, P_{t3})/2 \quad (32)$$

$$T_{te} = CR(P_{e5}, P_{e6})/2 \quad (33)$$

Alternatively, equations (34)–(45) can be used to determine the additional variables from the cross-correlation coefficients:

$$CR(P_{e3}, P_{e2}) = (4*T_{fe} + 4*T_{we}) - (2*T_{fe} + 2*T_{we}) \quad (34)$$
$$= 2*T_{fe} + 2T_{we}$$

$$CR(P_{e1}, P_{e3}) = (2*T_{fe} + 2*T_{we}) - (2*T_{fe}) \quad (35)$$
$$= 2*T_{we}$$

$$CR(P_{e1}, P_{e4}) = (4*T_{fe} + 4*T_{we}) - (2*T_{fe}) \quad (36)$$
$$= 2*T_{fe} + 4*T_{we}$$

$$CR(P_{e5}, P_{e6}) = (4*T_{te}) - (2*T_{te}) \quad (37)$$
$$= 2*T_{te}$$

$$CR(P_{t1}, P_{t2}) = (T_{fe} + T_{we} + T_s + 3*T_{wt} + 3*T_{ft}) - \quad (38)$$
$$(T_{fe} + T_{we} + T_s + T_{wt} + T_{ft})$$
$$= 2*T_{ft} + 2*T_{wt}$$

$$CR(P_{t1}, P_{t3}) = (T_{fe} + T_{we} + T_s + T_{wt} + 3*T_{ft}) - \quad (39)$$
$$(T_{fe} + T_{we} + T_s + T_{wt} + T_{ft})$$
$$= 2*T_{ft}$$

-continued $$CR(P_{t3}, P_{t2}) = (T_{fe} + T_{we} + T_s + 3*T_{wt} + 3*T_{ft}) - \qquad (40)$$
$$(T_{fe} + T_{we} + T_s + T_{wt} + 3*T_{ft})$$
$$= 2*T_{wt}$$

So:

$$T_{fe}=CR(P_{e3},P_{e4})-CR(P_{e1},P_{e4})/2=CR(P_{e3},P_{e4})/2-CR(P_{e1},P_{e3})/2 \quad (41)$$

$$T_{we}=CR(P_{e1},P_{e3})/2=CR(P_{e1},P_{e4})/2-CR(P_{e3},P_{e4})/2 \quad (42)$$

$$T_{ft}=CR(P_{t1},P_{t3})/2=CR(P_{t1},P_{t2})/2-CR(P_{t3},P_{t2})/2 \quad (43)$$

$$T_{wt}=CR(P_{t3},P_{t2})/2=CR(P_{t1},P_{t2})/2-CR(P_{t1},P_{t3})/2 \quad (44)$$

$$T_{te}=CR(P_{e5},P_{e6})/2 \quad (45)$$

Alternative Embodiments of the Present Invention

FIGS. 4a and 4b illustrate an alternative embodiment of the present invention for determining transit time and caliper of a sample. Essentially, the orifice reflective plate combinations in both tires 22 and 24 have been removed. Thus, the $P_{e5}$ and $P_{e6}$ echo pulses are no longer generated. Instead, two additional ultrasonic transducers 32a and 34a have been placed within the tires 22 and 24. Their sole function is the measurement of the two ultrasonic fluid velocities. Reflective plates 50 and 52 are affixed to each of these velocity transducers 32a and 34a, respectively, and are held apart from the transducer surface by offset rings 54 and 56 by an arbitrary known distance $D_{ve}$ within tire 22 and $D_{vt}$ within tire 24. These two velocity transducers 32a and 34a behave in essentially the same way as the transmitting ultrasonic transducer 32 emitting a short burst of ultrasonic energy and immediately thereafter operating in a listening mode to transform echoes resulting from that emission into electrical signals. As with pulses $P_{e5}$ and $P_{e6}$, the first and second echo pulses from the reflective plates, pulses $P_{v1}$ and $P_{v2}$ within tire 22 and $P_{v3}$ and $P_{v4}$ within tire 24 are digitized and cross-correlated to produce two ultrasonic transit times $T_{ve}$ and $T_{vt}$, respectively, which, in conjunction with the known distances $D_{ve}$ and $D_{vt}$, allow the determination of velocity of ultrasound within each tire, as set forth below in equations (46) and (47):

$$CR(P_{v1},P_{v2})=(4*T_{ve})-(2*T_{ve})=2*T_{ve} \quad (46)$$

$$CR(P_{v3},P_{v4})=(4*T_{vt})-(2*T_{vt})=2*T_{vt}, \quad (47)$$

where $V_{ve}=V_{fe}$ (the velocity of ultrasound through fluid in tire 22) is the distance $D_{ve}$ divided by the time $T_{ve}$, and $V_{vt}=V_{ft}$ (the velocity of ultrasound through the fluid in tire 24) is the distance $D_{vt}$ divided by $T_{vt}$.

This alternative method allows the simultaneous measurement of the upper and lower tire ultrasonic pulse propagation speeds through liquid at any time. In the embodiment of FIGS. 3a and 3b, a pulse propagation velocity through liquid could only be calculated within the currently transmitting tire 22. Moreover, the transducers 32 and 34 (FIGS. 3a and 3b) had to be arranged so that the receiving transducer 34 was reconfigured to be the transmitting transducer and the transmitting transducer 32 became the receiving transducer to measure the fluid velocity in the lower tire 24. Although the switching (receiver/transmitter to transmitter/receiver) could occur continuously during the ongoing measurement process in FIGS. 3a and 3b, the alternative embodiment shown in FIGS. 4a and 4b do not require such switching.

Figure 5A:
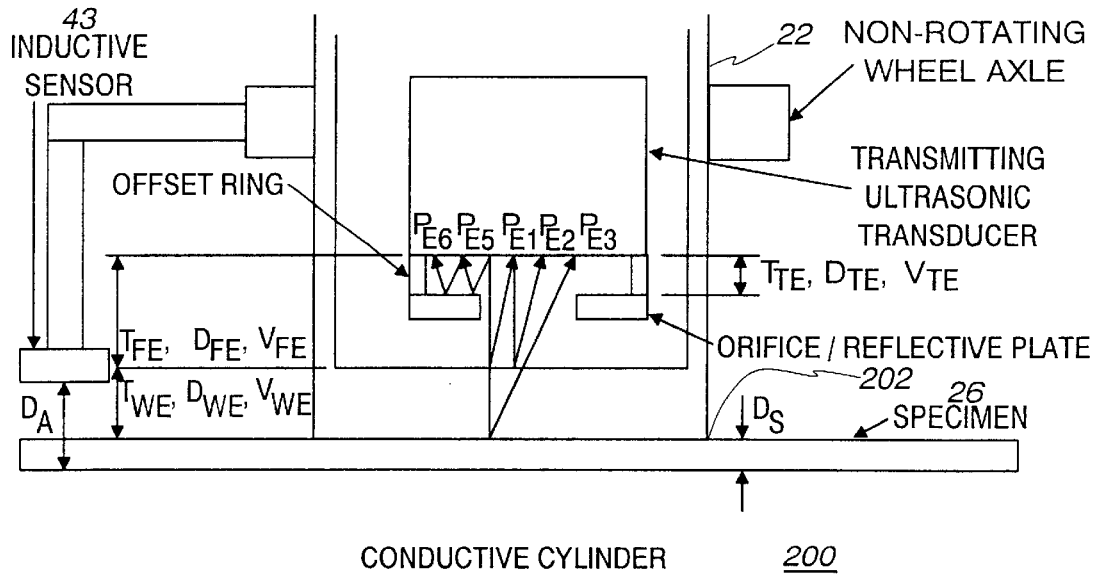
FIG. 5a is a schematic of another embodiment of the present invention employing a rotatable wheel and a conductive cylinder suitable for measuring specimen thickness (caliper)
Figure 5B:
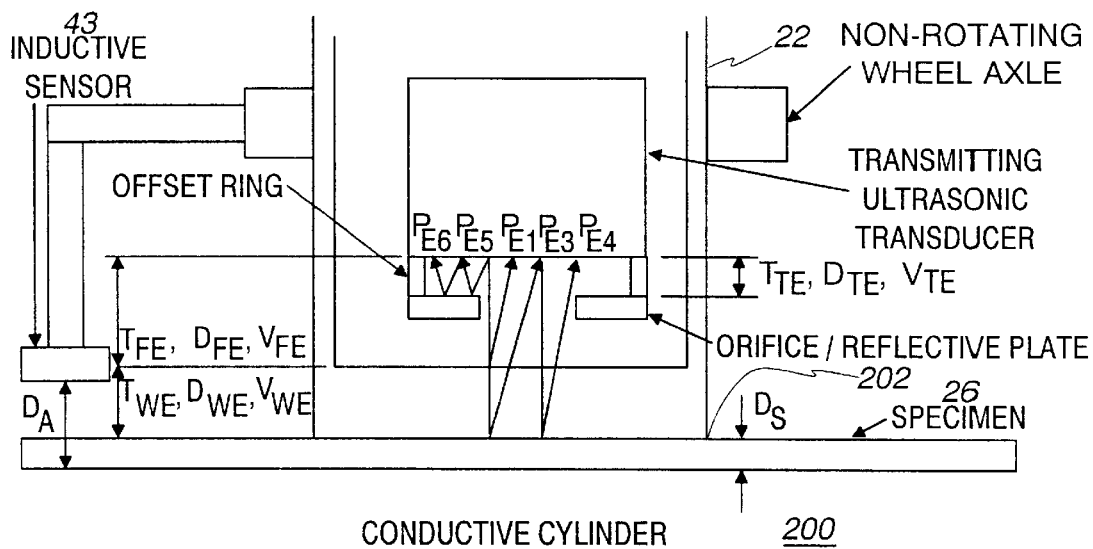
FIG. 5b is a schematic of the apparatus shown in FIG. 5a showing an alternative pulse set for measuring specimen thickness (caliper)
Figure 6A:
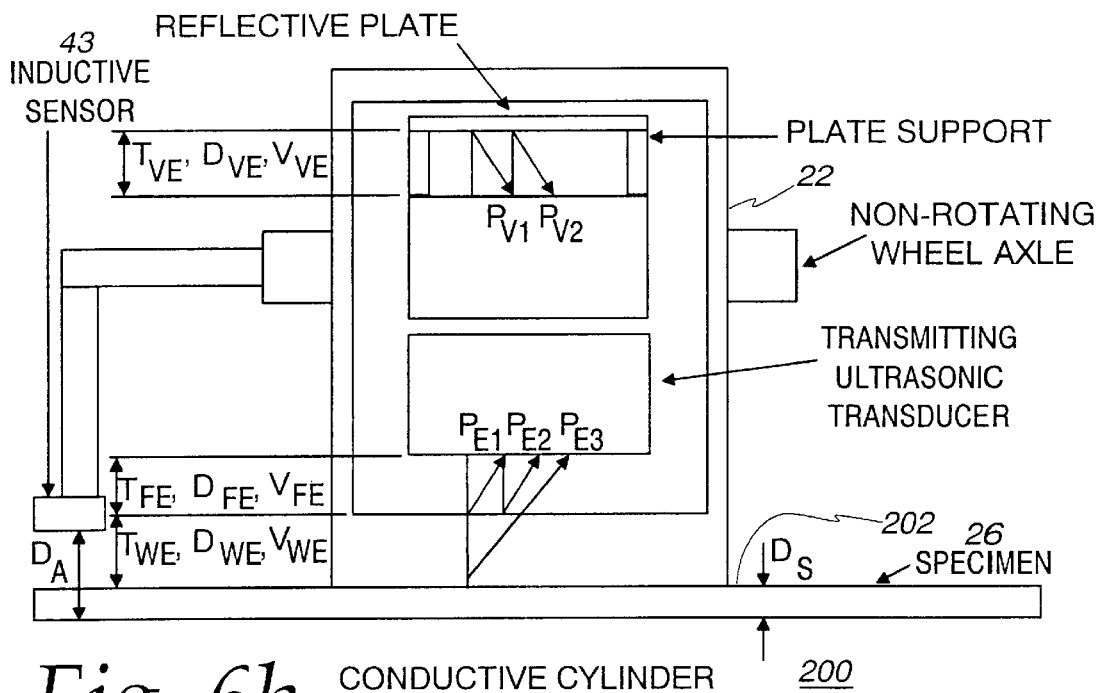
FIG. 6a is a schematic of another embodiment of the conductive cylinder type apparatus having a separate liquid pulse propagation cell within a wheel suitable for measuring specimen thickness.
Figure 6B:
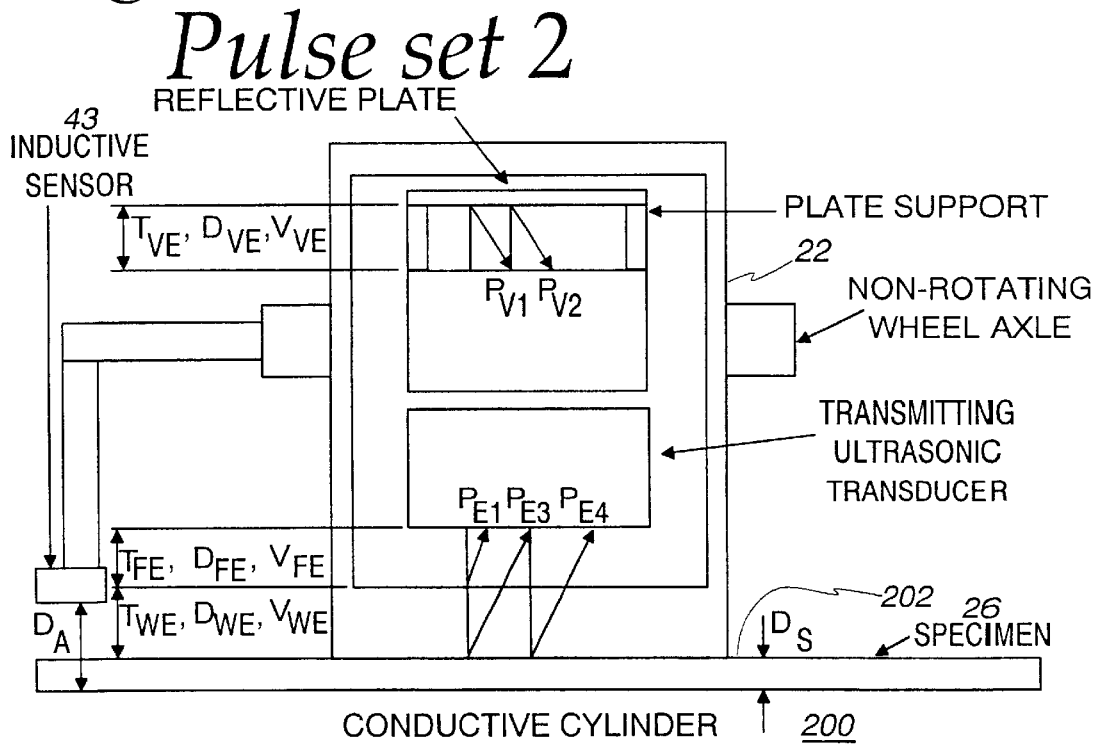
FIG. 6b is a schematic of the apparatus show in FIG. 6a showing an alternative set of pulses suitable for measuring specimen thickness.

In additional alternative embodiments, as an alternative to the two liquid-filled wheel apparatus, a fluid-filled wheel and a conductive rotating cylinder may be used as shown in FIGS. 5a, 5b, 6a, and 6b. FIGS. 5a and 5b represent one cylinder-tire embodiment having alternative pulse sets to choose in determining caliper of a sample. FIGS. 6a and 6b represent a second cylinder-tire embodiment having alternative pulse sets to choose in determining caliper of a sample.

Between the liquid-filled wheel 22 and a conductive rotating cylinder 200, a nip 202 is formed by the point of contact between the outer circumference of the wheel 22 and the outer circumference of a rotating conductive cylinder 200, which has an axis of rotation that is parallel to the fluid-filled wheel 22. The conductive cylinder 200 preferably has a diameter of at least several inches so that the nip 202 will constitute a reasonably close approximation to a flat plane. The inductive sensor 43 provides $D_a$, a measure of the distance between the conductive transducer and the outer circumference of the rotating cylinder 200 plus some arbitrary constant. The cylinder 200 must be conductive in order to provide a conductive target for the inductive sensor 43, similar to that which was described in the embodiments of FIGS. 2a–4b.

The determination of caliper for the sample 26 proceeds in exactly the same manner as in the previously described embodiments, with the exception that ultrasonic pulses, transit times, and path lengths associated with tire 24 (FIGS. 2a–4b) need not be determined. In this case, the measurement of the caliper of the specimen is attributable to displaced fluid path ($D_{fe}$) within the single fluid-filled wheel 22, as shown in FIGS. 5a–6b.

FIGS. 5a and 5b illustrate a single ultrasonic transducer apparatus. FIGS. 6a and 6b illustrate an equivalent dual ultrasonic transducer apparatus.

With the single transducer apparatus of FIG. 5a, the following equations (48)–(54) apply using pulse set 1:

$$CR(P_{e1}, P_{e2}) = (4*T_{fe}) - (2*T_{fe}) \quad (48)$$
$$= 2*T_{fe}$$

$$CR(P_{e1}, P_{e3}) = (2*T_{fe} + 2*T_{we}) - (2*T_{fe}) \quad (49)$$
$$= 2*T_{we}$$

$$CR(P_{e3}, P_{e2}) = (4*T_{fe}) - (2*T_{fe} + 2*T_{we}) \quad (50)$$
$$= 2*T_{fe} - 2*T_{we}$$

$$CR(P_{e5}, P_{e6}) = (4*T_{te}) - (2*T_{te}) \quad (51)$$
$$= 2*T_{te}$$

So:

$$T_{fe}=CR(P_{e1},P_{e2})/2=CR(P_{e3},P_{e2})/2+CR(P_{e1},P_{e3})/2 \quad (52)$$

$$T_{we}=CR(P_{e1},P_{e3})/2=CR(P_{e1},P_{e2})/2-CR(P_{e3},P_{e2})/2 \quad (53)$$

$$T_{te}=CR(P_{e5},P_{e6})/2 \quad (54)$$

With the single transducer apparatus of FIG. 5b, the following equations (55)–(61) apply using pulse set 2:

$$CR(P_{e3}, P_{e4}) = (4*T_{fe} + 4*T_{we}) - (2*T_{fe} + 2*T_{we}) \quad (55)$$
$$= 2*T_{fe} + 2*T_{we}$$

$$CR(P_{e1}, P_{e3}) = (2*T_{fe} + 2*T_{we}) - (2*T_{fe}) \quad (56)$$
$$= 2*T_{we}$$

-continued $$CR(P_{e1}, P_{e4}) = (4*T_{fe} + 4*T_{we}) - (2*T_{fe}) \quad (57)$$
$$= 2*T_{fe} + 4*T_{we}$$

$$CR(P_{e5}, P_{e6}) = (4*T_{te}) - (2*T_{te}) \quad (58)$$
$$= 2*T_{te}$$

So:

$$T_{fe}=CR(P_{e3},P_{e4})-CR(P_{e1},P_{e4})/2=CR(P_{e3},P_{e4})/2-CR(P_{e1},P_{e3})/2 \quad (59)$$

$$T_{we}=CR(P_{e1},P_{e3})/2=CR(P_{e1},P_{e4})/2-CR(P_{e3},P_{e4})/2 \quad (60)$$

$$T_{te}=CR(P_{e5},P_{e6})/2 \quad (61)$$

For the apparatus set forth in FIG. 6a, the following equations (62)–(68) apply using pulse set 1:

$$CR(P_{e1}, P_{e2}) = (4*T_{fe}) - (2*T_{fe}) \quad (62)$$
$$= 2*T_{fe}$$

$$CR(P_{e1}, P_{e3}) = (2*T_{fe} + 2*T_{we}) - (2*T_{fe}) \quad (63)$$
$$= 2*T_{we}$$

$$CR(P_{e3}, P_{e2}) = (4*T_{fe}) - (2*T_{fe} + 2*T_{we}) \quad (64)$$
$$= 2*T_{fe} - 2*T_{we}$$

$$CR(P_{v1}, P_{v2}) = (4*T_{ve}) - (2*T_{ve}) \quad (65)$$
$$= 2*T_{ve}$$

So:

$$T_{fe}=CR(P_{e1},P_{e2})/2=CR(P_{e3},P_{e2})/2+CR(P_{e1},P_{e3})/2 \quad (66)$$

$$T_{we}=CR(P_{e1},P_{e3})/2=CR(P_{e1},P_{e2})/2-CR(P_{e3},P_{e2})/2 \quad (67)$$

$$T_{ve}=CR(P_{v1},P_{v2})/2 \quad (68)$$

For the apparatus set forth in FIG. 6b, the following equations equations (69)–(75) apply using pulse set 2:

$$CR(P_{e3}, P_{e4}) = (4*T_{fe} + 4*T_{we}) - (2*T_{fe} + 2*T_{we}) \quad (69)$$
$$= 2*T_{fe} + 2*T_{we}$$

$$CR(P_{e1}, P_{e3}) = (2*T_{fe} + 2*T_{we}) - (2*T_{fe}) \quad (70)$$
$$= 2*T_{we}$$

$$CR(P_{e1}, P_{e4}) = (4*T_{fe} + 4*T_{we}) - (2*T_{fe}) \quad (71)$$
$$= 2*T_{fe} + 4*T_{we}$$

$$CR(P_{v1}, P_{v2}) = (4*T_{ve}) - (2*T_{ve}) \quad (72)$$
$$= 2*T_{ve}$$

So:

$$T_{fe}=CR(P_{e3},P_{e4})-CR(P_{e1},P_{e4})/2=CR(P_{e3},P_{e4})/2-CR(P_{e1},P_{e3})/2 \quad (73)$$

$$T_{we}=CR(P_{e1},P_{e3})/2=CR(P_{e1},P_{e4})/2-CR(P_{e3},P_{e4})/2 \quad (74)$$

$$T_{ve}=CR(P_{v1},P_{v2})/2 \quad (75)$$

Process for Determining Transit Time and Caliper

Now turning to FIGS. 7–12, the general operation of the system for determining transit time and caliper of a sample is shown in accordance with an exemplary embodiment of the present invention.

Figure 7:
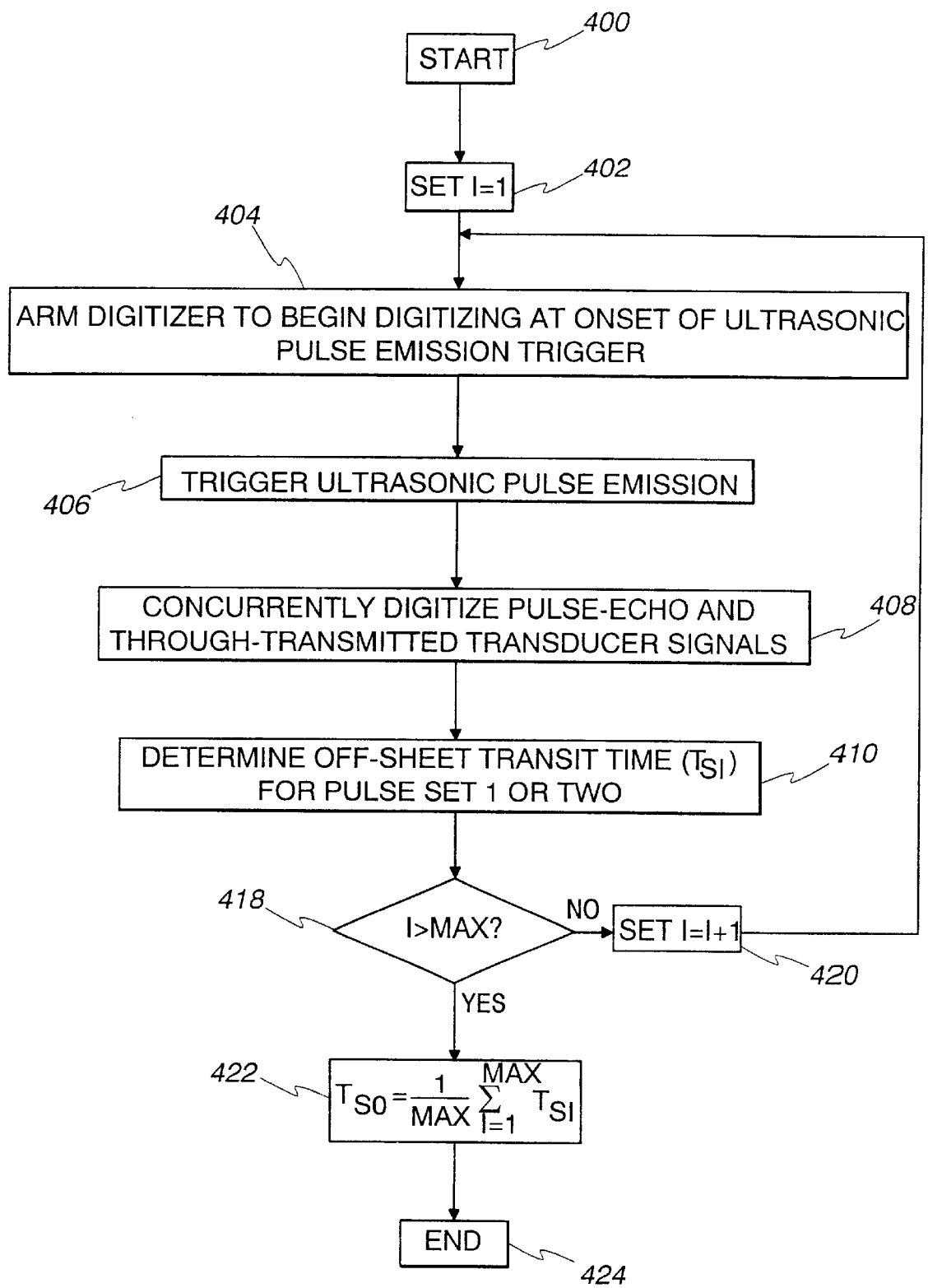
FIG. 7 is a flow diagram illustrating operation of the present invention in connection with standardizing the transit time measurement off-sheet.

In order to perform a standardized off-sheet measurement according to the equations set forth above in support of the measurement of ultrasonic transit time, referring to FIG. 7, the system 20 is started in step 400. A counter is initialized to be equal to 1, in step 402. Next, in step 404, the digitizer is armed to begin digitizing when a pulse is emitted. In step 406, the computer triggers an ultrasonic pulse emission from the ultrasonic pulser via the trigger generator. Concurrent digitization processes begin, in step 408. Next, the off-sheet transit time is determined for a specified pulse set 1 or 2, in accordance with equations (1)–(11).

In step 418, a determination is made as to whether the counter has reached a maximum. If a maximum has not been reached, the counter is incremented in step 420; otherwise, in step 422, an average is taken of all of the measurements, and the standardized off-sheet time $T_{sO}$ is determined. The process terminates in step 424.

Figure 8:
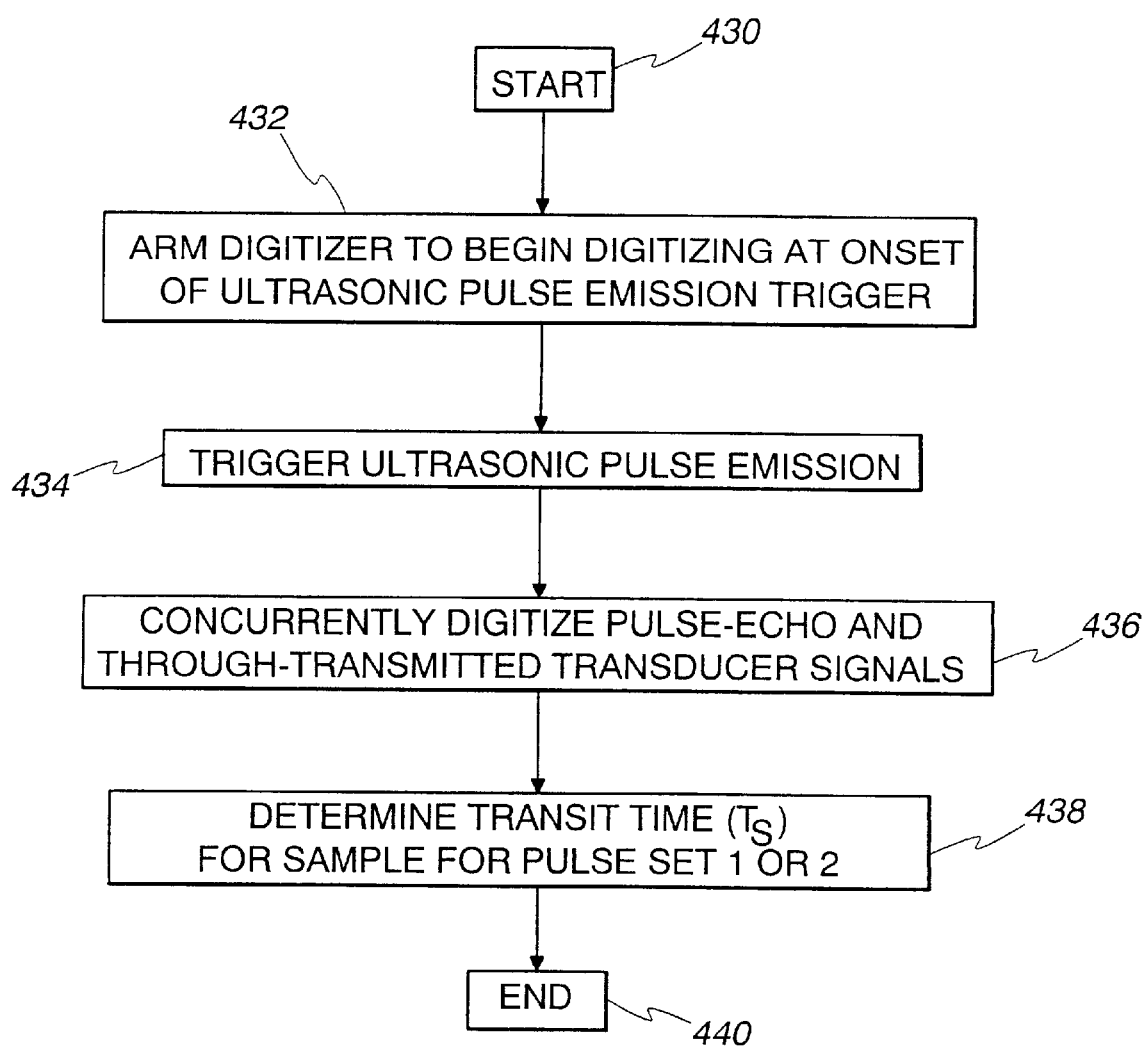
FIG. 8 is a flow diagram illustrating operation of the present invention in connection with measuring the transit time on-sheet.

After off-sheet standardization, the transit time may be measured on-sheet according to the process shown in FIG. 8. The process begins with the Start step 430. Again, the digitizer is armed to begin digitizing at the onset of an emitted pulse, in step 432. A pulse is emitted, in step 434. Next, in step 436, the echo pulses and through transmitted pulses are digitized. Using equations (1)–(11), in step 438, the transit time for the sample is then determined for the selected pulse set 1 or 2, depending on the pulse set used for standardization. The actual transit time for the sample is determined by taken into account the standardized off-sheet time $T_{sO}$, as previously described herein in connection with FIGS. 2a and 2b. The process terminates at the End step 440.

Figure 9:
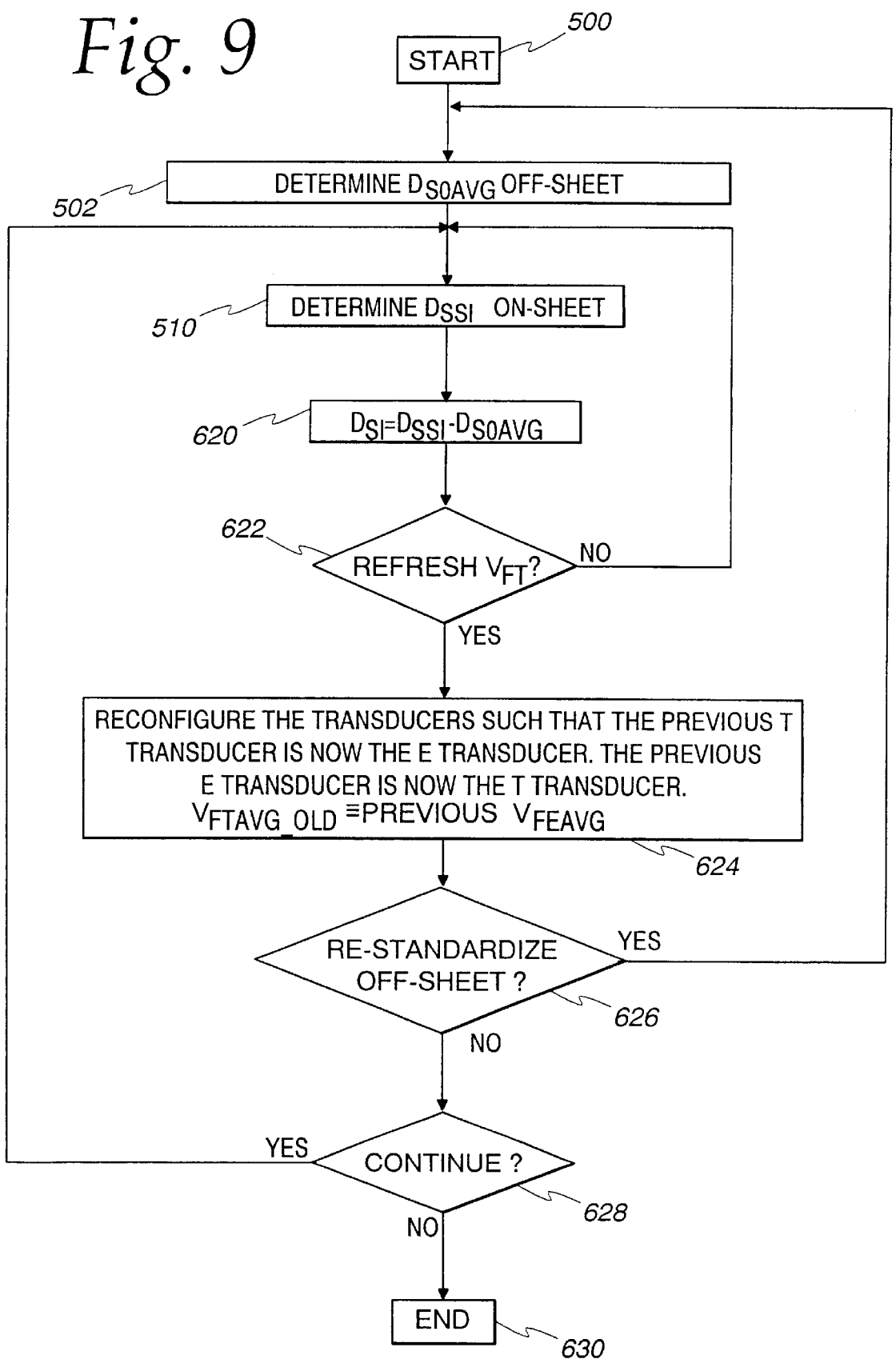
FIG. 9 is a flow diagram illustrating operation of the present invention in connection with determining the caliper measurement of a sheet in a two transducer environment.

Now turning to FIG. 9, the process for determining a specimen thickness (caliper) measurement in a two-transducer environment is described in accordance with the present invention. The process begins at the Start step 500. In step 502, the off-sheet caliper is determined. This process for measuring off-sheet caliper is described in greater detail herein below in connection with FIG. 10. Next, in step 510, the caliper is determined on-sheet. This determination includes sampling signals as described in connection with FIG. 11 below. Once the off-sheet caliper and on-sheet caliper are determined, the actual caliper for the sample is determined by taking the difference between the two caliper measurements, in step 620. The equations for caliper are provided above in association with FIGS. 3a–6b.

Next, $V_{ft}$ is tested for a refresh, in step 622. If the current liquid temperature is changing rapidly due to changing environmental conditions, then this refresh operation may be performed more often. The refresh is usually performed while on-sheet every few seconds or so. The transducers are then reversed, in step 624. Measurements may continue with this new configuration without the need of a new off-sheet standardization. In step 626, a determination is made whether to re-standardize off-sheet. If so, the "Yes" branch is followed to step 502, where the off-sheet caliper is again determined; otherwise, the "No" branch is followed to step 628. Off-sheet standardization needs to be performed only once, but may be performed more often as well. In step 628, a determination is made as to whether measurement is to continue. If so, the process is repeated beginning with step 510; otherwise, the process terminates at step 630.

Figure 10:
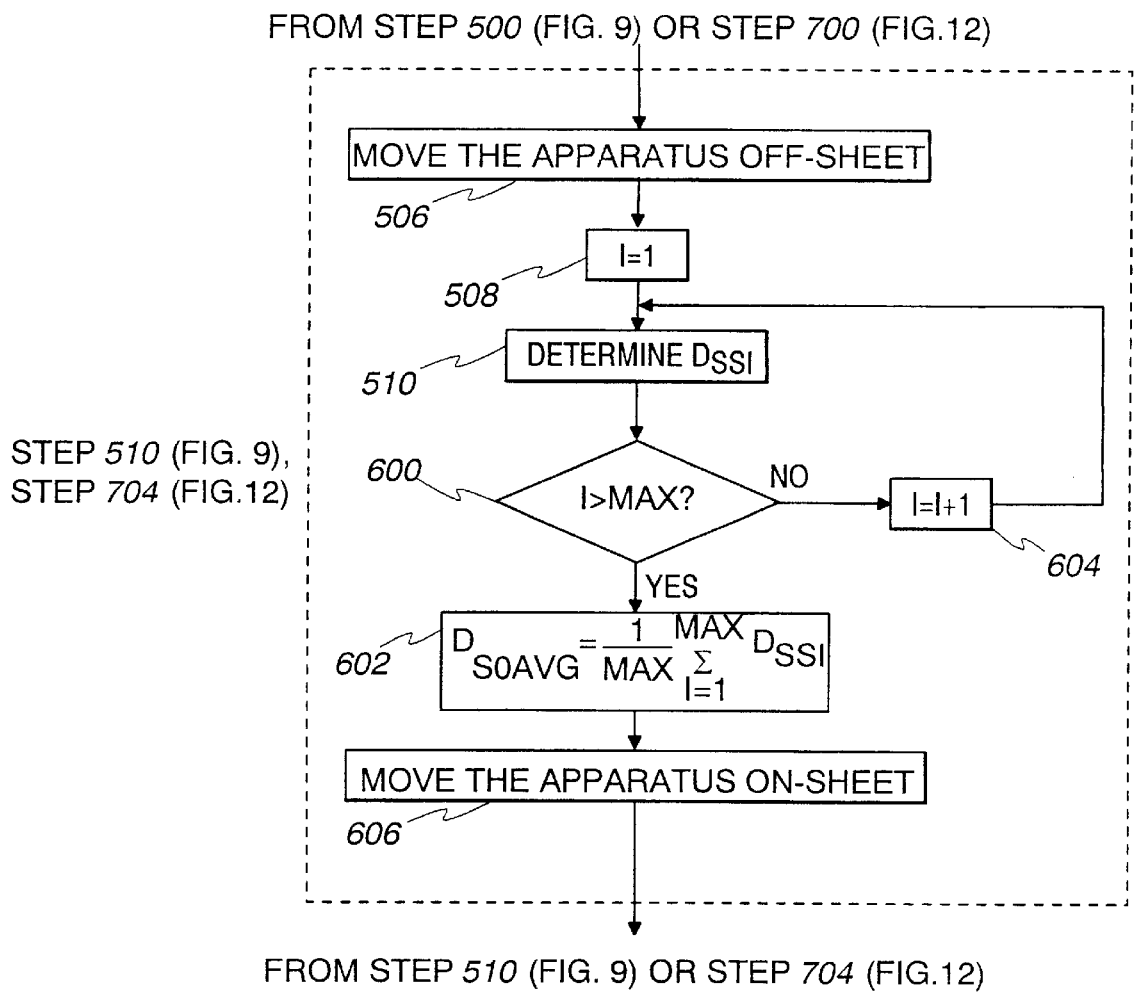
FIG. 10 is a flow diagram illustrating the determination of the average thickness of the tire off-sheet in a two and four transducers environment.

Now turning to FIG. 10, the process for determining off-sheet caliper (step 502 of FIG. 9 above and step 702 of FIG. 12 below) is illustrated. In step 506, the system is run with no sample present. A counter is initialized to be equal to 1, in step 508. Next, in step 510, the off-sheet caliper is determined for a specified pulse set 1 or 2, in accordance with equations (22)–(45).

In step 600, a determination is made as to whether the counter has reached a maximum. If a maximum has not been reached, the counter is incremented in step 604; otherwise, in step 602, an average is taken of all of the measurements, and the standardized off-sheet caliper $D_{s0avg}$ is determined. Next, in step 606, the system is moved on-sheet. The process then proceeds to either step 510 (FIG. 9) or step 704 (FIG. 12), depending on a two- or four-transducer environment, for determination of the caliper for a sample.

Figure 11:
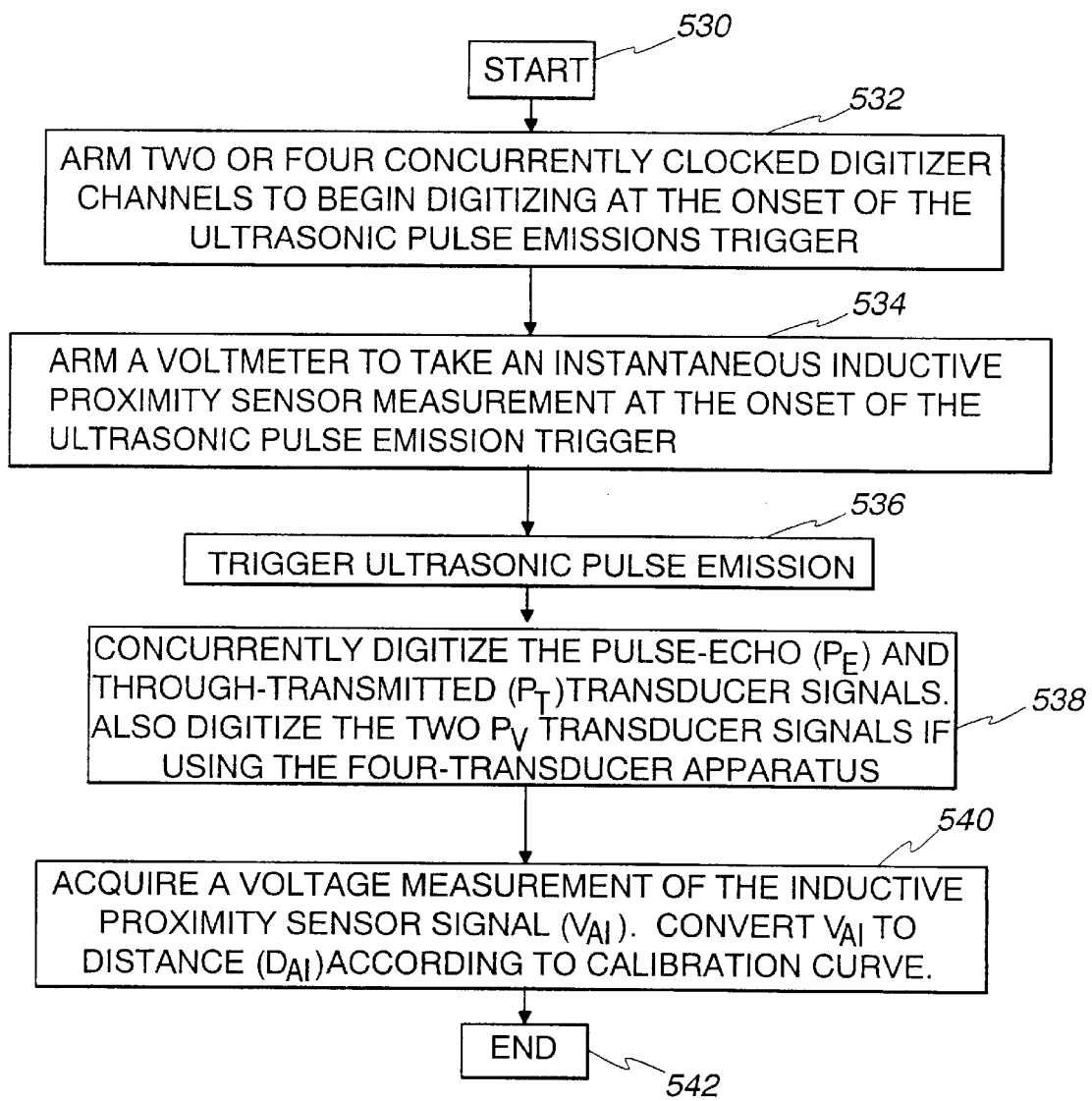
FIG. 11 is a flow diagram illustrating the process for sampling signals in accordance with a preferred embodiment of the present invention.

Referring now to FIG. 11, the process for sampling signals for use in determining on-sheet caliper is described in accordance with the present invention. The process begins with the Start step 530, and then proceeds to step 532, in which the digitizer channels are armed. At the onset of pulse emission the voltmeter is armed, in a step 534. Next, in step 536, the ultrasonic pulses are triggered. Pulse echoes and transmitted pulses are digitized, in step 538. A voltage measurement of the inductive sensor is converted to a distance via a calibration procedure, in step 540. The sampling process terminates at step 542.

Figure 12:
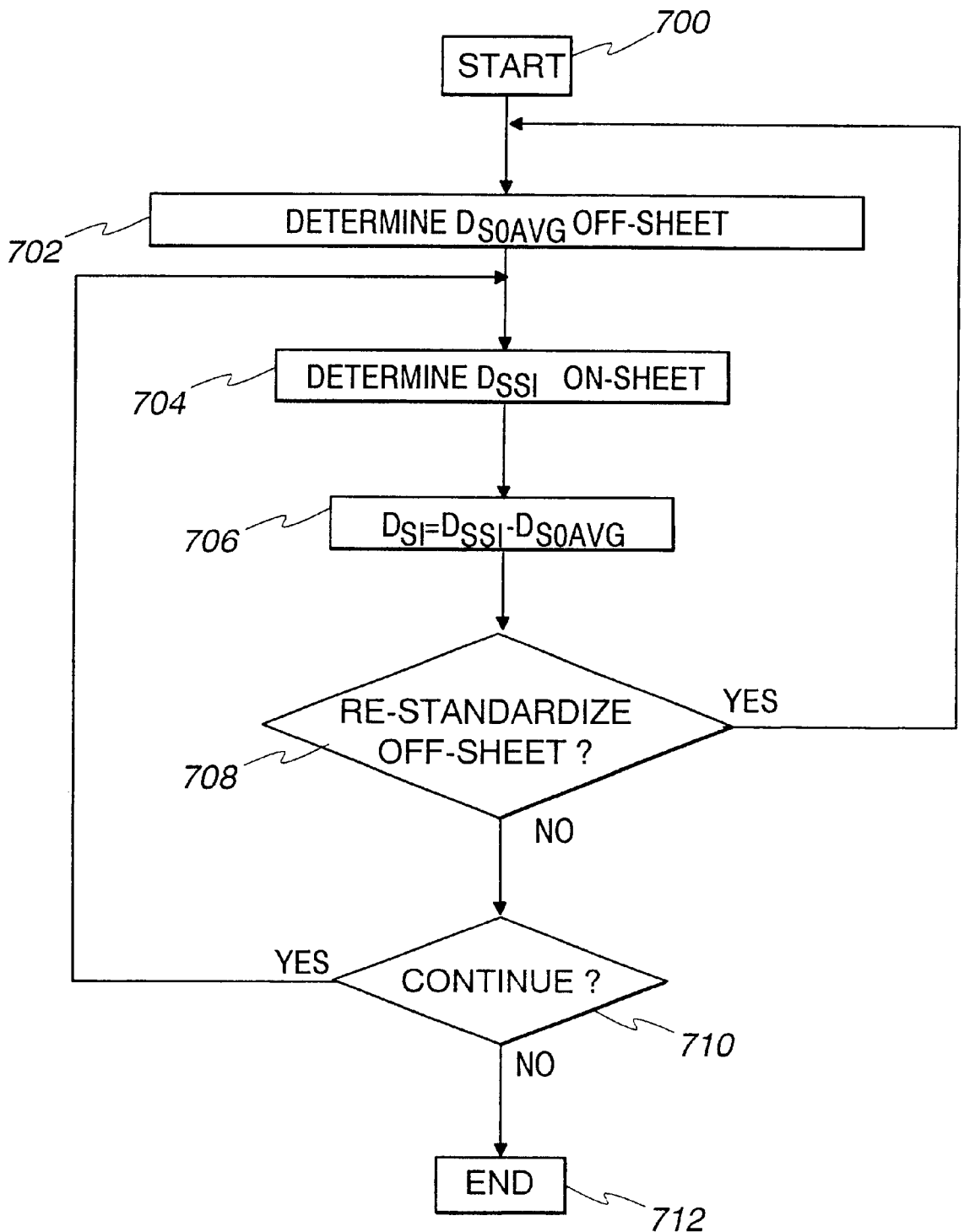
FIG. 12 is a flow diagram illustrating the process for determining the caliper measurement of a sheet in a four transducer environment.

Similar to the two-transducer environment, the process for measuring caliper in a four-transducer environment is described in connection with FIG. 12. The process begins at the Start step 700. The average apparent caliper off-sheet $D_{soavg}$ is determined, in step 702, which is further described in greater detail above in connection with FIG. 10. Next, the average apparent caliper on-sheet $D_{ssi}$ is determined, in step 704, as previously described above. This determination includes sampling signals as described in connection with FIG. 11 above. Once the off-sheet caliper and on-sheet calipers are determined, the actual caliper for the sample is determined by taking the difference between the two caliper measurements, in step 706. The equations for caliper are provided above in association with FIGS. 3a–6b. In step 708, a determination is made whether to re-standardize off-sheet. If so, the "Yes" branch is followed to step 702, where the off-sheet caliper is again determined; otherwise, the "No" branch is followed to step 710. In step 710, a determination is made as to whether measurement is to continue. If so, the process is repeated beginning with step 704; otherwise, the process terminates at step 712.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A method for determining the transit time of an ultrasonic pulse through a moving web of thin material using a rotatable wheel ultrasound apparatus, comprising:

measuring a transit time of a transit time ultrasonic pulse through a liquid within a rotatable tire of a rotatable wheel ultrasound apparatus;

determining a speed of ultrasound propagation from the transit time of the transit time ultrasonic pulse;

measuring a transit time of a wheel-reflected pulse from an interior surface of the rotatable tire at a liquid-tire boundary;

determining an instantaneous transducer-tire boundary distance from a speed of pulse propagation through the liquid and the liquid-tire boundary transit time;

measuring a transit time from a nip boundary at the outside of the rotatable tire; and determining an instantaneous tire wall thickness.

2. A method for determining the transit time of an ultrasonic pulse through a moving web of thin material using a rotatable wheel ultrasound apparatus according to claim 1, further comprising determining a transit time through the moving web of thin material.

3. A method for determining the transit time of an ultrasonic pulse through a moving web of thin material using a rotatable wheel ultrasound apparatus according to claim 1, further comprising determining a thickness of the moving web of thin material.

4. A method for determining the transit time of an ultrasonic pulse through a moving web of thin material using a rotatable wheel ultrasound apparatus according to claim 1, further comprising determining a speed of propagation through a liquid in a second rotatable tire filled with a liquid which is adapted to engage the rotatable tire.

5. Apparatus for determining a transit time of an ultrasonic pulse through a moving web of thin material, comprising:

a rotatable wheel having an ultrasonic transducer immersed in a liquid, the wheel having an outer surface for engaging a moving web of thin material whose properties are to be measured;

a reflector of ultrasound positioned within the wheel and immersed in the liquid to reflect at least a portion of an ultrasonic pulse back to the ultrasonic transducer; and a circuit associated with the transducer for timing a time of propagation from a time the ultrasonic pulse is emitted by the ultrasonic transducer to a time when the pulse reflected by the reflector is received to provide a transit time of the pulse through the liquid.

6. Apparatus for determining a transit time of an ultrasonic pulse through a moving web of thin material according to claim 5 wherein the circuit associated with the ultrasonic transducer determines a transmission time through the moving web of thin material.

7. Apparatus for determining a transit time of an ultrasonic pulse through a moving web of thin material according to claim 5 wherein the circuit determines a specimen caliper.

8. Apparatus for determining a transit time of an ultrasonic pulse through a moving web of thin material according to claim 5 further comprising:

a second rotatable wheel at a second ultrasonic transducer immersed in a liquid, the second wheel having an outer surface for engaging the sample whose properties are to be measured; and a second reflector of ultrasound positioned within the second wheel and immersed in the liquid to reflect at least a portion of an ultrasonic pulse back to the second ultrasonic transducer, the second ultrasonic transducer being coupled to the circuit, the circuit providing timing of the propagation from the time the ultrasonic pulse is emitted by the second ultrasonic transducer to a time when the pulse reflected by the second reflector is received by the second ultrasonic transducer to provide a transit time of the pulse through the liquid.

9. Apparatus for determining a transit time of an ultrasonic pulse through a moving web of thin material, comprising:

a rotatable wheel having an ultrasonic transducer immersed in a liquid, the wheel having an outer surface for engaging a sample whose properties are to be measured;

a reflector of ultrasound positioned within the wheel and immersed in the liquid to reflect at least a portion of an ultrasonic pulse back to the transducer;

a circuit associated with the transducer for timing a time of propagation from a time the ultrasonic pulse is emitted by the transducer to a time when the pulse reflected by the reflector is received to provide a transit time of the pulse through the liquid; and a second wheel filled with liquid and having a second ultrasonic transducer therein, the second ultrasonic transducer receiving at least a portion of the pulse from the second transducer from which a time of flight is determined, the time of flight being indicative of a property of the sample between the wheels.

10. Apparatus for determining a transit time of an ultrasonic pulse through a moving web of thin material according to claim 9 wherein the circuit determines a transit time of an ultrasonic pulse through the moving web of thin material.

11. Apparatus for determining a transit time of an ultrasonic pulse through a moving web of thin material according to claim 9 wherein the circuit determines a specimen caliper of the moving web of thin material.

12. Apparatus for determining a transit time of an ultrasonic pulse through a moving web of thin material according to claim 9 wherein the second wheel has positioned therein a second reflector of ultrasound to reflect at least a portion of an ultrasonic pulse back to the second transducer determining a speed of propagation of ultrasonic pulses through the liquid in the second wheel.

13. Apparatus for determining a transit time of an ultrasonic pulse through a moving web of thin material, comprising:

a rotatable wheel having an ultrasonic transducer immersed in a liquid, the wheel having an outer surface for engaging a sample whose properties are to be measured;

a reflector of ultrasound positioned within the rotatable wheel and immersed in the liquid to reflect at least a portion of an ultrasonic pulse back to the ultrasonic transducer;

a circuit associated with the ultrasonic transducer for timing a time of propagation from the time the ultrasonic pulse is emitted by the ultrasonic transducer to a time when the pulse reflected by the reflector is received to provide a transit time of the pulse through the liquid; and a rotatable cylinder that reflects the pulse back to the ultrasonic transducer, a time of flight of the pulse reflected from the rotatable cylinder being indicative of a property of the sample between the wheel and the cylinder.

14. Apparatus for determining the transit time of an ultrasonic pulse through a moving web of thin material according to claim 13 further comprising a cylinder wheel displacement measuring apparatus for inductively measuring displacement between the rotatable wheel and the rotatable cylinder.

15. Apparatus for determining the transit time of an ultrasonic pulse through a moving web of thin material according to claim 13 wherein the circuit determines a specimen transit time through the moving web of thin material.

16. Apparatus for determining the transit time of an ultrasonic pulse through a moving web of thin material according to claim 13 wherein the circuit determines the specimen caliper.

* * * * *

UNITED STATES PATENT AND TRADEMARK OFFICE
CERTIFICATE OF CORRECTION

PATENT NO. : 6,308,570 B1
DATED : October 30, 2001
INVENTOR(S) : Jackson et al.

It is certified that error appears in the above-identified patent and that said Letters Patent is hereby corrected as shown below:

Column 23,
Line 22, after the word "transducer" insert the word -- for --.

Signed and Sealed this

Twenty-fourth Day of December, 2002

JAMES E. ROGAN
*Director of the United States Patent and Trademark Office*